(12) United States Patent
Elmasry

(10) Patent No.: US 11,904,084 B2
(45) Date of Patent: Feb. 20, 2024

(54) ULTRAPORTABLE AND ADJUSTABLE NOSE, EAR, AND WOUND ASPIRATOR AND IRRIGATOR DEVICE AND RELATED METHODS

(71) Applicant: Medhat N. Elmasry, Hillsville, VA (US)

(72) Inventor: Medhat N. Elmasry, Hillsville, VA (US)

( * ) Notice: Subject to any disclaimer, the term of this patent is extended or adjusted under 35 U.S.C. 154(b) by 334 days.

(21) Appl. No.: 17/120,165

(22) Filed: Dec. 12, 2020

(65) Prior Publication Data
US 2022/0184282 A1 Jun. 16, 2022

(51) Int. Cl.
*A61M 1/00* (2006.01)

(52) U.S. Cl.
CPC ....... *A61M 1/74* (2021.05); *A61M 2205/3365* (2013.01); *A61M 2205/8206* (2013.01); *A61M 2205/8237* (2013.01); *A61M 2210/0618* (2013.01); *A61M 2210/0662* (2013.01)

(58) Field of Classification Search
CPC ........ A61M 1/0058; A61M 1/60; A61M 1/63; A61M 1/74; A61M 1/76; A61M 1/77; A61M 1/80; A61M 1/85; A61M 1/90; A61M 1/772; A61M 31/00; A61M 2205/50; A61M 2205/3365; A61M 2205/8206; A61M 2205/8237; A61M 2210/0618; A61M 2210/0662; A61M 2005/14513; A61H 35/04
See application file for complete search history.

(56) References Cited

U.S. PATENT DOCUMENTS

| | | | | |
|---|---|---|---|---|
| 5,496,299 A * | 3/1996 | Felix | ........................ | A61M 1/77 604/319 |
| 7,959,597 B2 * | 6/2011 | Baker | ................. | A61M 3/0212 604/28 |
| 8,414,521 B2 * | 4/2013 | Baker | ..................... | A61M 1/77 604/35 |
| 9,433,724 B2 * | 9/2016 | Rubin | ................. | A61M 3/0283 |
| 9,463,271 B2 * | 10/2016 | Cane' | ................. | A61M 5/1413 |
| 2002/0161317 A1 * | 10/2002 | Risk | ..................... | A61M 1/743 602/2 |
| 2008/0065083 A1 * | 3/2008 | Truckai | .............. | A61B 17/8811 600/407 |
| 2008/0154183 A1 * | 6/2008 | Baker | ................... | A61M 1/772 604/28 |
| 2008/0208112 A1 * | 8/2008 | Bensoussan | ............ | A61M 1/80 604/35 |
| 2009/0281482 A1 * | 11/2009 | Baker | ..................... | A61M 1/77 604/35 |
| 2014/0121592 A1 * | 5/2014 | Rubin | ..................... | A61M 1/77 604/35 |
| 2016/0262459 A1 * | 9/2016 | Monsees | .................. | H05B 3/42 |

(Continued)

*Primary Examiner* — Benjamin J Klein
*Assistant Examiner* — Jihad Dakkak

(57) ABSTRACT

An aspiration and irrigation ultraportable device is disclosed. The device is configured to aspirate and irrigate alone or sequentially. The device comprises a digitally adjustable dry/wet vacuum and a spray/irrigator assembly that is powered by rechargeable batteries. The device has at least one easily disposable and cleanable aspirant/irrigant reservoir. The present invention relates to the field of medicine specially related to outpatient and in-home settings of aspiration and irrigation of nose, ear, open wounds, and other body fluids.

21 Claims, 20 Drawing Sheets

(56) References Cited

U.S. PATENT DOCUMENTS

| | | | |
|---|---|---|---|
| 2016/0331913 A1* | 11/2016 | Bourque | A61M 15/0043 |
| 2018/0296753 A1* | 10/2018 | Lange | A61M 5/14248 |
| 2019/0060565 A1* | 2/2019 | Gyory | A61M 5/148 |
| 2019/0184088 A1* | 6/2019 | Mechor | A61M 11/008 |
| 2020/0164155 A1* | 5/2020 | Mojarrad | A61M 5/19 |
| 2020/0315914 A1* | 10/2020 | Naygauz | A61J 1/2096 |

* cited by examiner

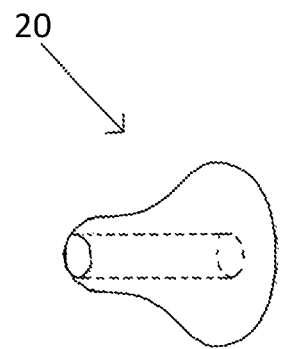
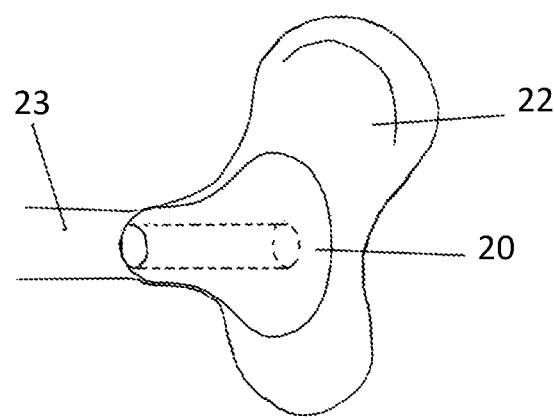
Fig. 11

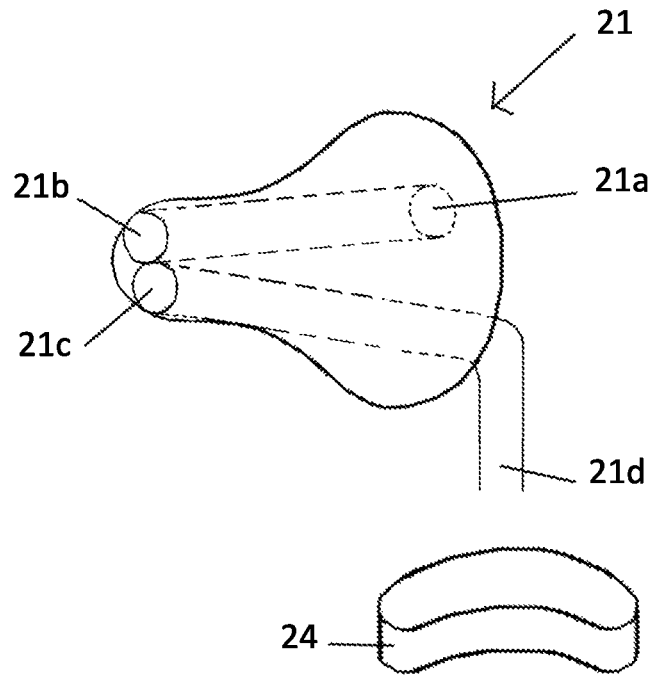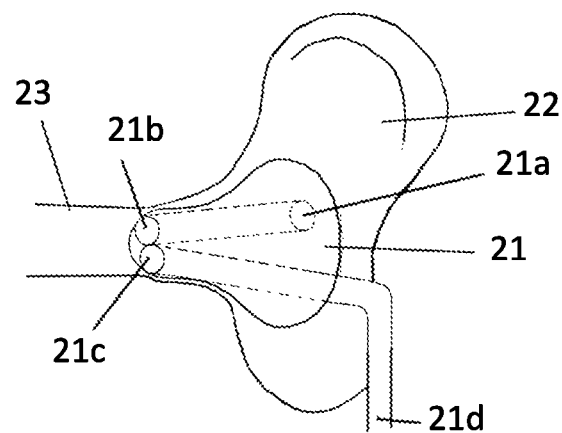
Fig. 12

ULTRAPORTABLE AND ADJUSTABLE NOSE, EAR, AND WOUND ASPIRATOR AND IRRIGATOR DEVICE AND RELATED METHODS

FIELD OF THE INVENTION

The present device relates to an aspirator and irrigator device that can be used for the nose, ear, and wounds that is both portable and adjustable. In an embodiment, the device is configured to either aspirate and irrigate alone or to perform them sequentially. In an embodiment, the device comprises a digitally adjustable dry/wet vacuum and a spray/irrigator assembly that is powered by rechargeable batteries. The device has at least one easily disposable and cleanable aspirant/irrigant reservoir. The present invention relates to the field of medicine specifically related to outpatient and in-home settings of aspiration and irrigation of nose, ear, open wounds, and other body fluids.

BACKGROUND OF THE INVENTION

The human body has many natural defenses that allow a human being to ward off foreign matter and organisms. These natural defenses include the skin, the immune system (which is quite complicated), and secretions of the human body (such as mucus and ear wax) that aid in removing these foreign matter and organisms and the like. There are instances where the human body may be overwhelmed by the introduction of foreign matter and/or organisms, which can lead to severe consequences such as infections, orifice blockages, gangrene, other disabilities and/or even potentially death as well as other potential problems. One way to mitigate these consequences is to take action as soon as possible after the introduction of these foreign matters/organisms. One such means of action includes the irrigation and/or aspiration of places where foreign matter/organisms may be introduced, including but not limited to the ear, the nose, and open wounds that occur on the body.

Different hospitals, health clinics, and health workers have varied abilities to handle irrigation and/or aspiration of the above mentioned parts of the human body. Some of this variation may be due to the equipment that is possessed by the hospitals, health clinics, and/or health workers (or others who may perform these procedures). Places that are poor or that are in remote locations may not have adequate equipment to perform irrigation and/or aspiration. Additionally, because speed of treatment of individual patients may ultimately be a life saver, health workers such as EMTs (or other people who may perform these procedures) or those health workers in remote locations (including medics in war zones) might benefit from a device that allows them to perform irrigation and/or aspiration. A device that is very portable, that is relatively inexpensive, and that is relatively easy to use would be useful for these people.

There are some products that have been developed that combine an aspirator device and a spray device in the same instrument. Most of these powered portable nose and ear aspirators and/or irrigators require the user to detach the spray device first to attach the aspirator device onto the instrument and do not offer adjustable, strong enough vacuum/irrigation. Most of the devices of the prior art do not operate in an inverted position and the amount of fluid that can be aspirated by such devices is very limited and does not exceed a few milliliters in most of these devices. This is mostly attributed to the limited capacity of the aspirate/irrigant reservoir. Most of these devices have one or more of a plurality of drawbacks such as being bulky, difficult to clean, difficult to reassemble after detachment, and/or other drawbacks.

There has not been any portable, easy to use, and cost-effective device for nasal and ear aspiration and/or lavage that can be used by both the public and the medical community.

1. Nasal Aspirator and Irrigation:

Nasal congestion and discharge whether caused by infection or environmental allergies are amongst the most common symptoms of diseases and irritations in all age groups. Nasal and postnasal discharge have been among the main reasons patients diagnosed with sinusitis progress and develop ear infections, chest infections, as well as the exacerbation of asthma and sleep disorder symptoms. In addition, nasal and sinus discharge usually result in pain, nasal cavity blockage, headaches, and considerable discomfort. Nasal aspiration and irrigation have been shown to relieve symptoms and signs of rhinitis, sinusitis and to minimize the progression and the complication of sinusitis. It is desired that a device be generated that would minimize the economic impact of patient's sick time and possibly contribute to a safer/greener environment by reducing the use of disposable facial tissues.

2. Cerumen Removal and Ear Lavage:

Cerumen impaction and ear debris are among the major reasons for conductive hearing deficit. Also, cerumen impaction had been shown to predispose patients to ear infections and Eustachian tube dysfunction. In addition, cerumen removal/lavage is a must for hearing aids to function properly. When dealing with issues that relate to cerumen (earwax) and debris in the ears, others have used rigid objects in an attempt to clean the external auditory/ear canal. However, using rigid objects may result in injury with unpredictable results. Others have tried using softer objects to clean the ear, which mostly causes further cerumen (earwax) and debris impacting rather than removal of the wax. Thus, having a very portable, easy to use, and inexpensive device to be used in these instances would be very useful.

Moreover, it is desired to have a device that will readily irrigate and aspirate fluids contained in the external ear canal after diving, swimming and showering to minimize the chances of developing acute ear infections such as otitis external, otitis media, and conditions known as swimmers' ear.

3. Aspiration and Irrigation of Open Wounds.

Open wounds that occur often have dirt, debris, shrapnel, organic matter, bacteria, viruses, or other matter that appear in the wound that may potentially create long term adverse effects for a patient that suffers from said wound. These wounds may be infected wounds, incised abscesses, ulcers, burn wounds, surgical wounds, or other wounds. Thus, in an embodiment, it is desired to have a device that can clean and remove the matter from these open wounds at a time that is not long after the wound(s) occur(s).

It is with these drawbacks and considerations in mind that the present invention has been developed.

SUMMARY OF THE INVENTION

The present invention relates to an ultraportable, easy to operate, economical device that can both irrigate and aspirate different parts/orifices of the human body. The device of the present invention can perform irrigation and/or aspiration either alone, sequentially, or simultaneously (when controller box 100 houses two containers/reservoirs 10) without disassembling the device. The device is easy to clean, easy to replace the relatively large reservoir/container, easy to control, operates in inverted as well as upright positions, and is relatively inexpensive. In an embodiment, the device is designed to be used on the ear, nose, or open wounds, and there may be attachments that come with the device that make the device suited for that purpose. The device may come as a kit that allows the device to be used for any of these plurality of purposes.

BRIEF DESCRIPTION OF THE SEVERAL VIEWS OF THE DRAWINGS

FIG. 11 shows a cross sectional view of an ear conduit and a view of the conduit inserted in an ear.

FIG. 12 shows another embodiment with a cross sectional view of an ear conduit with a basin and with the ear conduit inserted in an ear.

DETAILED DESCRIPTION OF THE INVENTION

Figure 1:
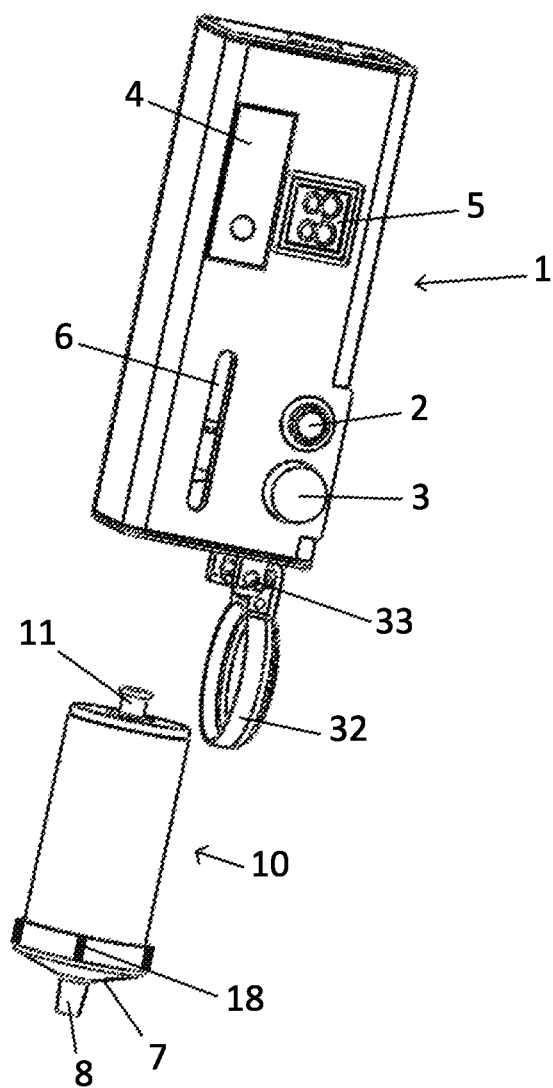
FIG. 1 shows a perspective view of the controller box and the reservoir/container.

The present invention relates to an ultraportable, easy to operate, economical device that can both irrigate and aspirate ear canals, nasal passages, and open wounds and other body parts. The present invention is more favorable to users because it is ultraportable, easy to operate, economical, and does not require detachment or disassembly of the aspirator to perform its dual functions of suction and ejection. Cleaning and removal of aspirated materials does not require detachment of the fluid containing compartment and can be performed instantly by ejection of aspirated fluids. In an embodiment, the device is self-cleaning without detachment of the various parts. In an embodiment, the device operates by applying multiple suctions and ejections of cleaning and/or disinfectant fluid. The syringe-like reservoir/container is disposable and may be replaced with one or more sterile or non-sterile containers/reservoirs. The replacement of these one or more sterile or non-sterile containers/reservoirs may be made by operator's choice and the respective one or more sterile or non-sterile containers/reservoirs that are used are based on the application(s) for which the device is used. Furthermore, in an embodiment, the suction and ejection functions may be digitally controlled by the operator. This renders the device safer because it is adjustable to the purpose it is used for, to the operators' desire, and to the subject's comfort. In an embodiment, the device does not use any fans to generate vacuum, and instead uses an air pump powering a syringe type of reservoir/container to generate accelerated suction/ejection with fewer moving parts. One additional and significant feature of the present invention is that it operates in any position including an inverted position. This is superior to the devices of the prior art in that most of them only operate or function in an upright position. Moreover, unlike the devices of the prior art, this device is easier to operate and maintain because it is less bulky, and it is less complicated with fewer moving parts. For example, it does not require one-way valves, nor does it require separate aspiration and ejection channels or pathways. Moreover, the device of the present invention is advantageous in that the capacity of the reservoir/container is considerably larger relative to other portable aspirator and irrigator devices. The device's sizable capacity allows for multiple suctions/aspirations before one need empty/eject the aspirated contents.

The present invention, in one embodiment, is related to treatment devices for open or incised wounds and methods that utilize a negative pressure therapy device for treatment of the same. The present invention relates, among other things, to a device and method for wound therapy that are capable of aspirating and irrigating a variety of chronic and acute open wounds including, but not limited to, infected wounds, incised abscesses, ulcers, burn wounds, surgical wounds, and the like.

In one embodiment, the device may be used for the aspiration of contents of incised abscess. Incising abscess to release its pustular contents combined with the use of antibiotics are the gold standards of treating abscesses. In a hospital setting, and in operating room, aspiration of incised abscesses, or infected wounds, bleeding sites, are ideally achieved using catheters attached to central vacuuming. In contrast, in an outpatient setting, the procedure of incision and draining of an abscess involves evacuating the pustular contents of the abscess, after being incised, by applying pressure to squeeze the abscessed area. This is done to achieve the maximum possible discharge and drainage of the contents of the abscess. Such squeezing process inflicts considerable pain and discomfort on the patient and increases the risk and likelihood of spreading the infection directly to adjacent areas of the lesion (local dissemination) and distally through blood stream (systemic dissemination).

The present device that uses a sterile nozzle or conduit, allows physicians to have a more effective, speedy, and easy to use portable, cost effective device to evacuate contents of an incised abscess with minimal to no pain to patients. The aspiration is achieved without risking the spread of the infection whether locally or distally. More importantly, the syringe container of the device is designed so that it may be disinfected by repeated aspiration and ejection of disinfectant. Alternatively, the operator, at will and per the operator's discretion, may dispose of the syringe container and replace it with another sterile syringe container.

In an alternate embodiment, the device of the present invention can be used in a similar way to irrigate open wounds. Current practice for irrigating open wounds is to use sterile sponges and/or gauze to remove discharge and/or blood from the open wounds, which is usually painful to the patient and is likely to cause or exacerbate bleeding. Irrigating such wounds by pouring sterile water or disinfectants in the open wound to wash away pustular contents, blood clots, debris, or contaminants tends to be less effective, and very labor intensive.

The device of the present invention provides a superior way of aspirating and irrigating open wounds and specifically removing pustular discharge from infected wounds without any of the complications and side effects stated above when using manual pressure, sponges, gauze, and irrigation. Moreover, the targeted irrigating ability of the device of the present invention as well as the aspirating aspect of the present invention provides superior results to simply pouring sterile water or disinfectants into the open wound.

In an embodiment, the present invention relates to an ultraportable, easy to operate, economical device that can both irrigate and aspirate ear canals and nasal passages. In an embodiment, the aspirating device does not require detachment and/or disassembly to perform either its dual functions of suction and ejection.

In an embodiment, the cleaning and removal of aspirated materials does not require detachment and/or disassembly of the fluid containing compartment and can be performed instantly by ejection of aspirated fluids. In a further embodiment, the device is self-cleaning and this self-cleaning can be performed without detachment of the device by applying multiple suctions and ejections of cleaning and/or disinfectant fluid. The syringe like reservoir/container is disposable and may be replaceable or replaced with sterile or non-sterile container/reservoir per operator's choice according to the applications for which the device is used. Furthermore, in an embodiment, the suction and ejection functions are digitally controlled by the operator. This renders the device safer because it is adjustable to the purpose it is used for, to the operators' desire, and to the subject's comfort. In an embodiment, the device does not use any fans to generate a vacuum. Rather, in an embodiment, it uses an air pump powering a syringe type of reservoir/container to generate accelerated suction/ejection with fewer moving parts. Unlike prior devices, the device of the present invention is easy to operate and maintain because it is less cumbersome and bulky, less complicated with very few moving parts, does not require one-way valves, nor does it require separate aspiration and ejection channels or pathways. In an embodiment, the capacity of the container is of a significant size for an ultraportable device that far exceeds the size of other portable aspirator and irrigator devices. The device's relatively large capacity allows for multiple suctions/aspirations before any need to empty/eject the contents, thereby allowing irrigation and aspiration to happen more quickly, and with fewer complications.

The present invention is described with reference to the figures.

Figure 2:
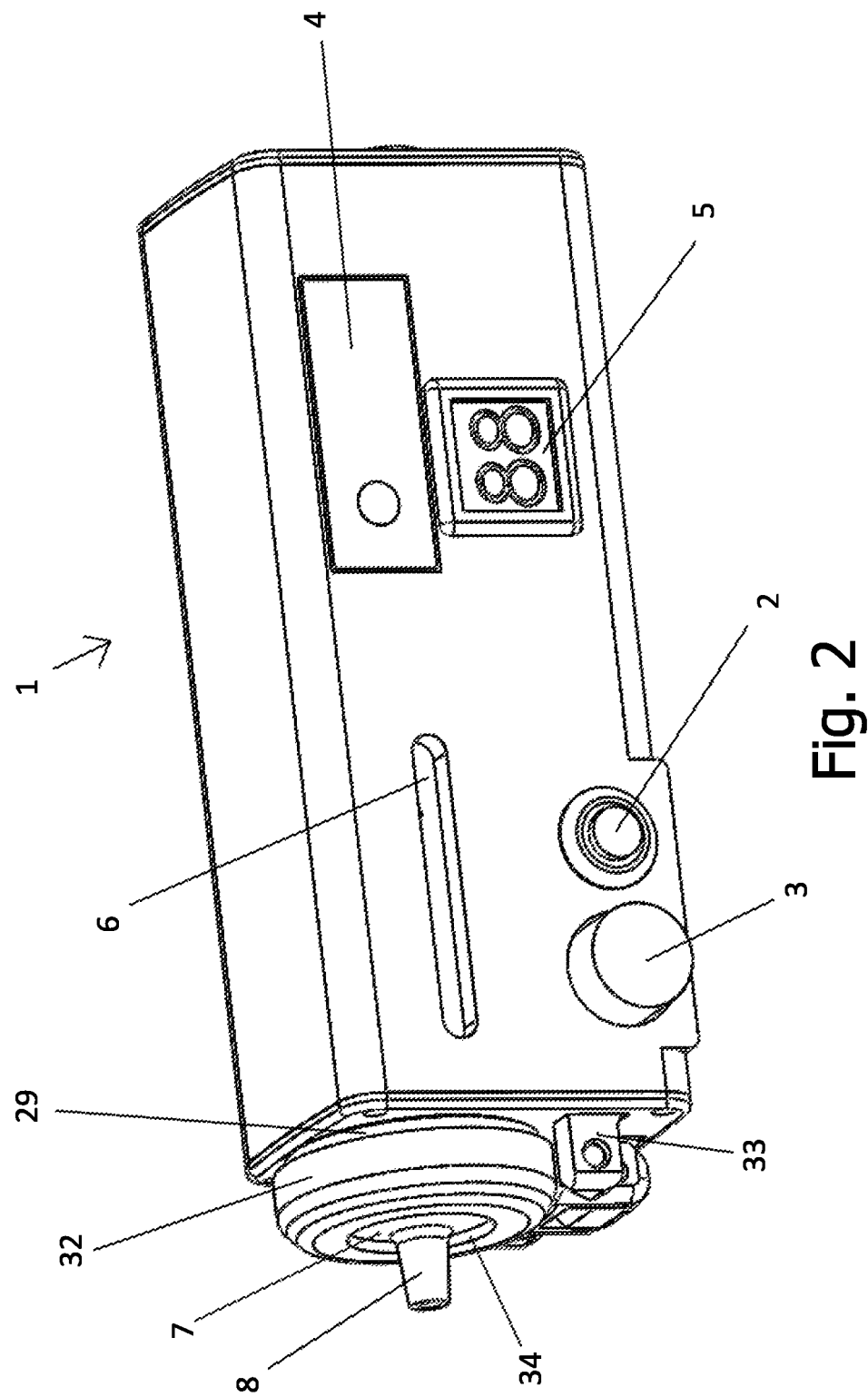
FIG. 2 shows a first side perspective view of the reservoir/container inserted in the controller box.
Figure 3:
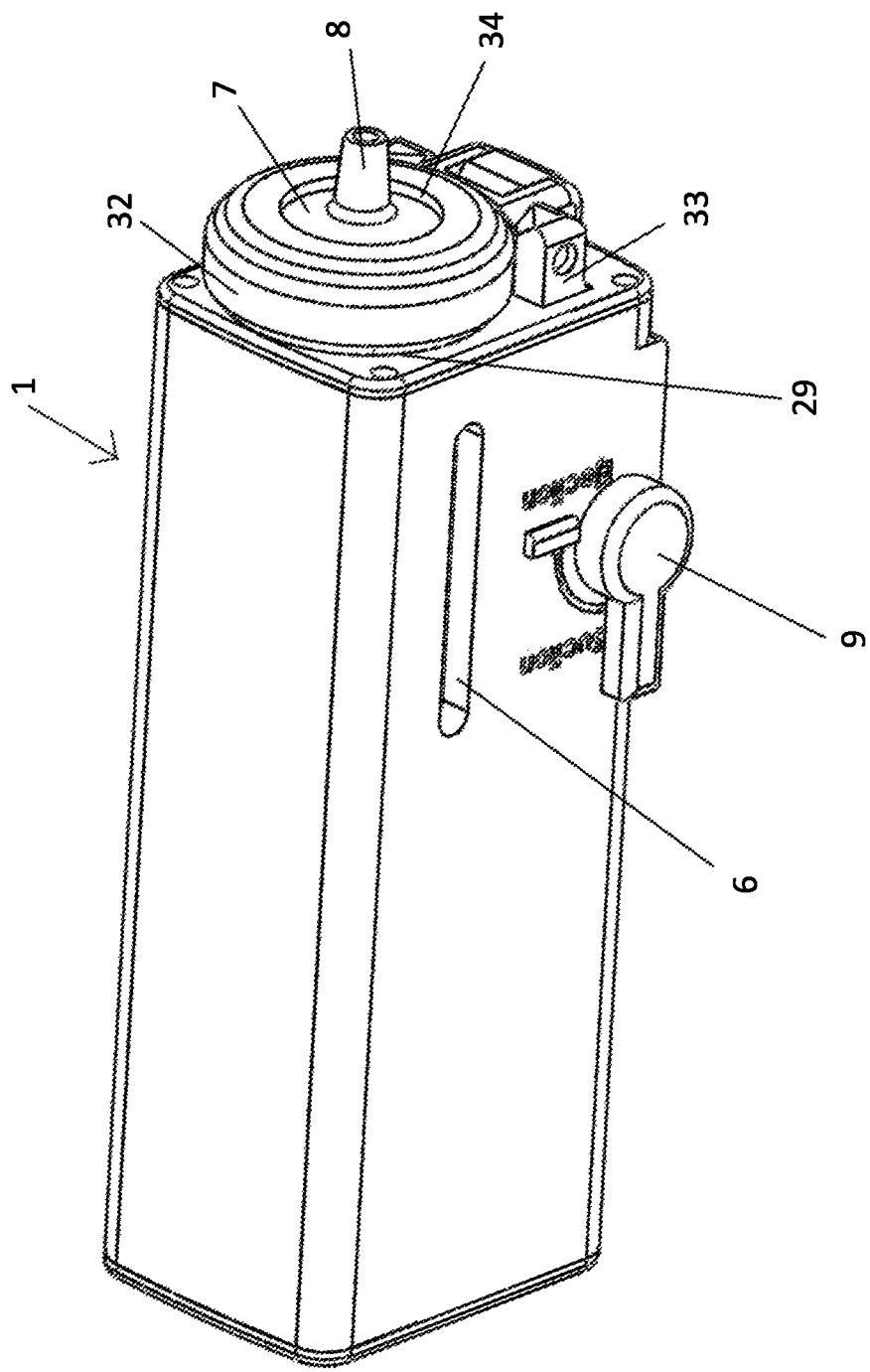
FIG. 3 shows a second side front perspective view of the reservoir/container inserted in the controller box.
Figure 4:
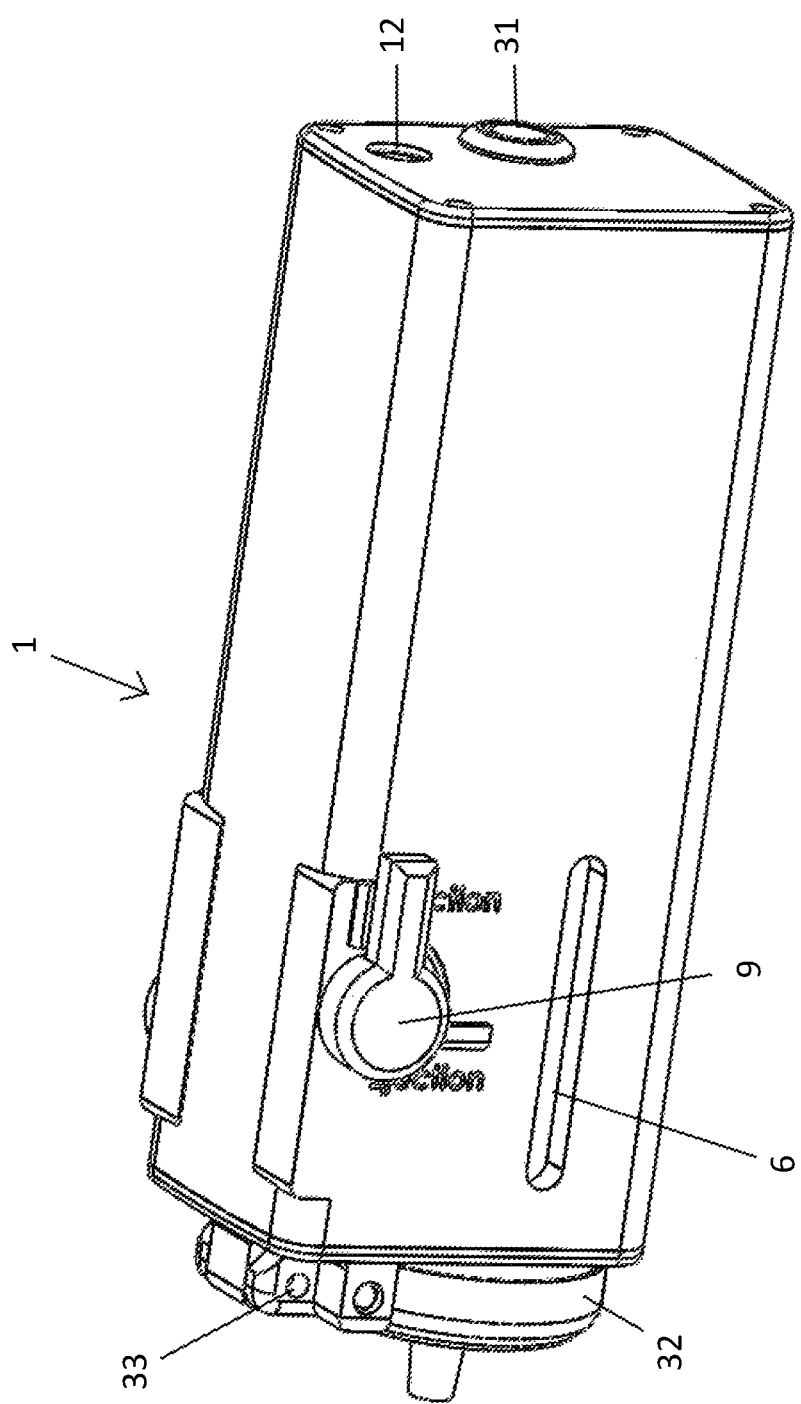
FIG. 4 shows a second side back perspective view of the reservoir/container inserted in the controller box.
Figure 5:
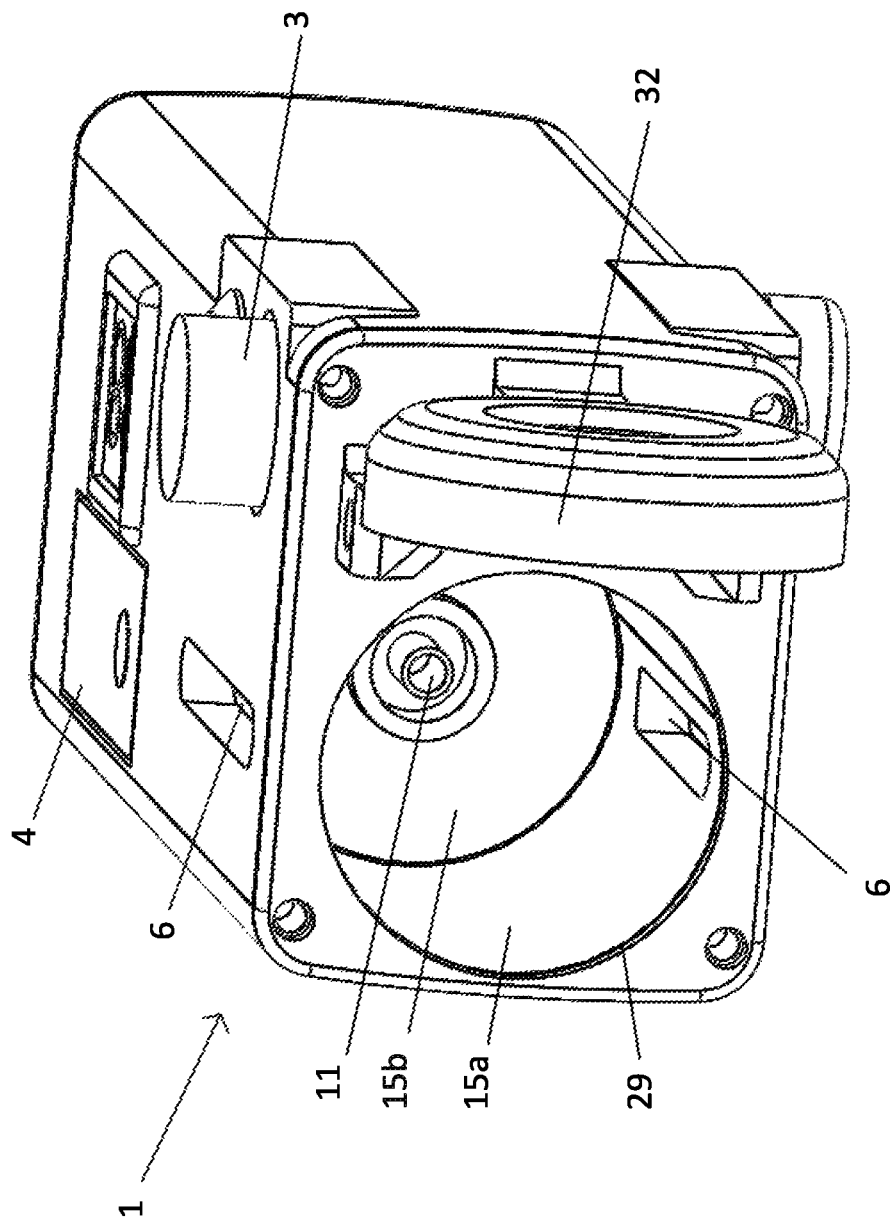
FIG. 5 shows a front and first side perspective view of the controller box with the flap open.

FIG. 1 shows a perspective view of one embodiment of the present invention. In this view, one will note that the device is comprised of two main parts: a 1) controller box 1 that is designed to hold 2) container/reservoir 10. The controller box 1, in one embodiment, is designed to be essentially a rectangular cuboid that is roughly 2 inches (50-55 mm) by 2 inches (50-55 mm) by 6 inches (150-160 mm). The container/reservoir 10, in an embodiment, is smaller than the controller box 1 so that it can readily fit inside the controller box 1. The controller box 1 has a spherical opening 29 on one end of the rectangular cuboid (best seen in FIGS. 2 and 5) that is designed to accommodate the container/reservoir 10, and once the container/reservoir 10 is inserted in the spherical opening 29 of the rectangular cuboid controller box 1, the container/reservoir 10 is able to operationally attach to the controller box 1 using a luer lock 11 (best seen in FIG. 5). The container/reservoir 10, in one embodiment is generally cylindrical in shape with a nozzle/conduit 8 on one end and a luer lock 11 positioned on and operationally connected to end cap/syringe cover 15*b* (see FIG. 6) on the other end. It should be understood that other shapes for the container/reservoir are contemplated, such as rectangular cuboid. By inserting the container/reservoir 10 in a direction wherein the luer lock 11 is inserted first in the spherical opening 29, the luer lock 11, in one embodiment, comprises a luer lock female 11*a* that is designed to attach to a fixed luer lock male 11*b* (seen in FIGS. 6, 7, and 8) that is operationally attached to machine syringe interface mount 17 that is positioned on the inside of the controller box 1 at a position so that when the luer lock female 11*a* engages the fixed luer lock male 11*b*, a portion of the container/reservoir 10 that comprises the nozzle/conduit 8 is still outside the controller box 1 (as seen in FIGS. 2, 3, and 4). End cap/syringe cover 15*b* (see FIGS. 5 and 6) can be any of a plurality of designs so that negative or positive pressure that is present in the controller box 1 allows a piston 30 (see FIG. 6), which is present inside the container/reservoir 10 to move in a direction that is towards the luer lock 11 or towards the nozzle/conduit 8, respectively.

The piston 30 is designed to fit snuggly inside the container/reservoir 10 so that no air escapes around the circumference of the piston 30. The end cap/syringe cover 15*b* can have any of a plurality of designs, with the understanding that the end cap/syringe 15*b* must have a structure that 1) allows for negative or positive pressure in the controller box 1 and 2) allows this negative or positive pressure to pass the end cap/syringe cover 15*b* allowing the piston 30 to move in a direction towards the luer lock 11 or towards the nozzle/conduit 8, respectively. Accordingly, in one embodiment, air can pass through the luer lock 11 into the container/reservoir so that the pressure that is present in the controller box is the same as the pressure that is in the area that is in the container/reservoir above the piston 30. When negative pressure is created by the pump, the piston moves in a direction towards the luer lock 11 and air and/or fluid can be drawn into the container/reservoir, and when the pump creates positive pressure, the piston moves towards the conduit and air and/or fluid is ejected from the container/reservoir. Alternatively, the end cap/syringe cover 15*b* may have perforations or holes in it that allows this negative or positive pressure to move the piston 30. Alternatively, the end cap/syringe cover 15*b* might have a design similar to the spokes on the rim of a bicycle wheel with the luer lock 11 attached at what would be the axle of the bicycle rim and the spokes holding the luer lock in place yet at the same time allowing the negative or positive pressure to occupy the space in the container/reservoir 10 that allows piston 30 to move towards the luer lock 11 (allowing fluid to aspirated/sucked in) or towards the nozzle/conduit 8 (ejecting fluid). In another embodiment, the luer lock 11 may have a passage way associated with it that allows the passage of air from the inside of the container/reservoir 10 to the controller box 1 and vice versa (i.e., passage of air in the other direction) thereby allowing and/or causing the piston 30 in the inside of the container/reservoir 10 to move.

It should be noted that in order for the device to work properly, the controller box 1, which contains a pump in it must be essentially air tight so that a negative or positive pressure can be effectively generated inside the controller box 1. Accordingly, the device should be sufficiently well made so as to assure tight fits of the parts, not allowing air to escape into the controller box (negative pressure in the controller box) or out (positive pressure in the controller box) of the controller box 1. In an embodiment, appropriate rubber or plastic gaskets may be present in various places to provide a sufficiently air tight fit so that the controller box 1 can maintain pressure. In an alternate embodiment, the negative or positive pressure that is generated may be confined to an air-tight compartment or vessel that resides in the controller box 1 that is operationally connected to the container/reservoir 10 allowing the piston 30 to move by generating a positive or negative pressure inside this compartment or vessel.

In an embodiment, the controller box 1 has associated with it a digitally adjustable air pump 13 that is operationally connected to a suction/ejection switch 9, which allows one to move the switch to generate positive (ejection) or alternatively, negative (suction) pressure in the controller box 1. In one embodiment, the container/reservoir may be of a size that is about thirty milliliters (30 ml) although others are contemplated and therefore within the scope of the invention. It has been found that a 30 ml container 10 works well and fits comfortably within a controller box 1 that has dimensions that are on the order of 2"×2"×6" (50 mm×50 mm×150 mm). Accordingly, if other size containers 10 are to be used, the size of the controller box may be adjusted accordingly to better accommodate those containers/reservoirs.

Figure 10:
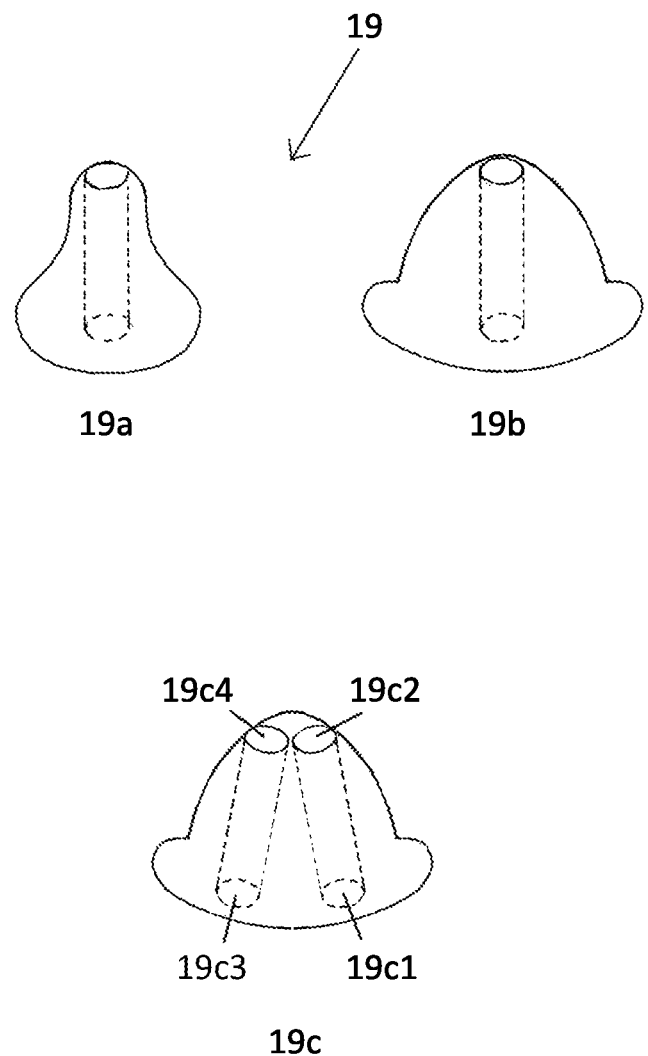
FIG. 10 shows a cross sectional view of different embodiments of nasal conduits.
Figure 14:
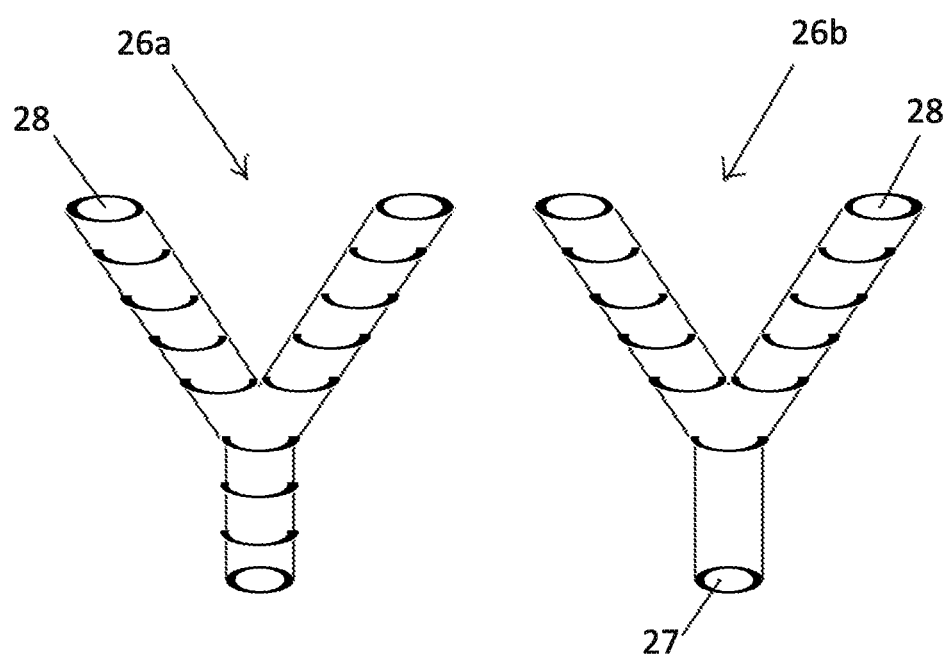
FIG. 14 shows cross sectional embodiments of two embodiments of dual nasal conduits.

The nozzle/conduit 8 can be fitted with removable sterile or non-sterile components that are especially designed for the purpose that they are to be used. In an embodiment, nasal conduits 19a and 19b (see FIG. 10) can be used that are designed to fit in the nostrils of a patient. The nasal conduits are designed to attach to the nozzle/conduit 8 that is present at one end of the container/reservoir 10. Similarly, dual nasal conduits 26a and 26b (FIG. 14) are designed to be able to lavage the nose by having a "y" shape that allows each of passageway 28 fit in each of the nostrils with the other end 27 attaching to the nozzle/conduit 8 that is present at one end of the container/reservoir 10. If the device is to be used for ear irrigation and lavage, one might use ear conduits 21 (FIG. 12) in order to irrigate the ear. Ear conduits 21 have channels that are illustrated by 21a, 21b, 21c, and 21d that allow the passage of fluids through them. As shown in FIGS. 1 and 12, the nozzle/conduit 8 from the container/reservoir 10 (in FIG. 1) attaches to the channel at channel point 21a (in FIG. 12) and fluid passes from inside the container/reservoir 10 through the nozzle/conduit 8 and into entering channel 21a and comes out at 21b into the external auditory canal 23 of the ear 22. The fluid, in one embodiment, will clean the external auditory canal 23 and because the fluid continues to increase in volume in the external auditory canal 23, it will exit the external auditory canal 23 through exiting canal 21c, can comes out at 21d, which can be collected in a basin 24. This process has the effect of cleaning the external auditory canal. In an embodiment, it should be understood that the fluid might be any fluid including saline, water, baby oil, mineral oil, glycerin or hydrogen peroxide that is initially introduced into the external auditory canal 23 in order to soften any crusty cerumen. In one embodiment, this fluid might be warmed a little bit prior to introduction to the external auditory canal 23 so as to better soften the cerumen.

Figure 6:
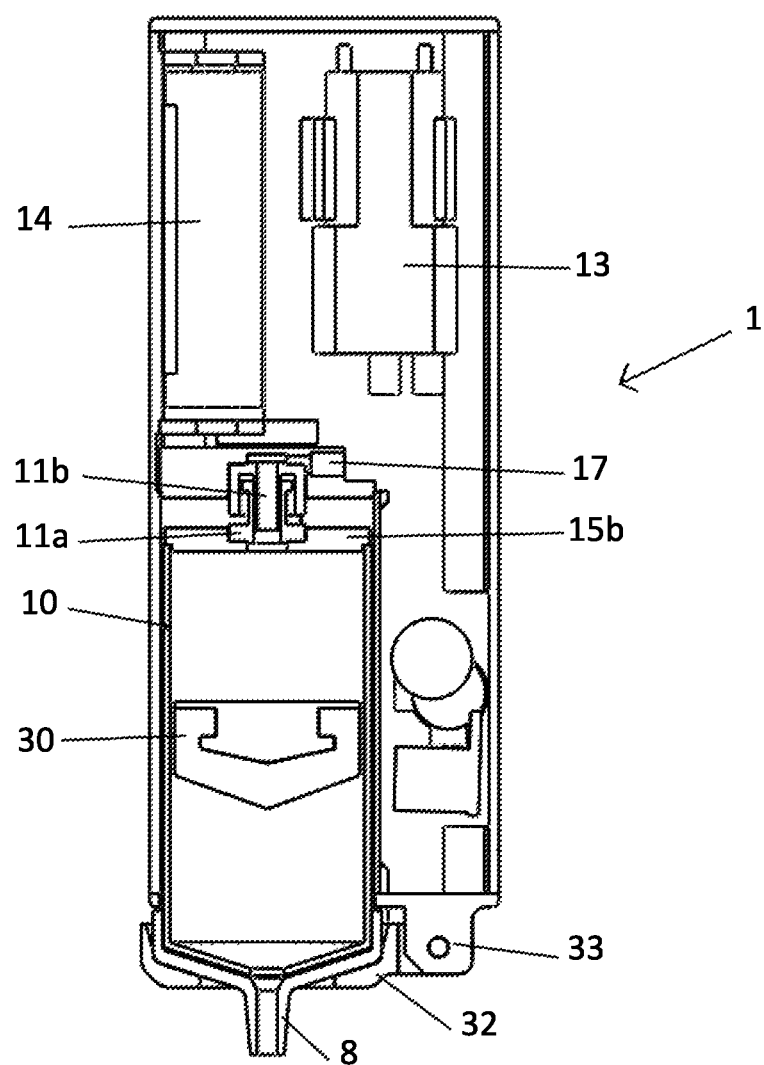
FIG. 6 shows a cross-sectional view of the controller box with the reservoir/container inserted in the controller box.
Figure 7:
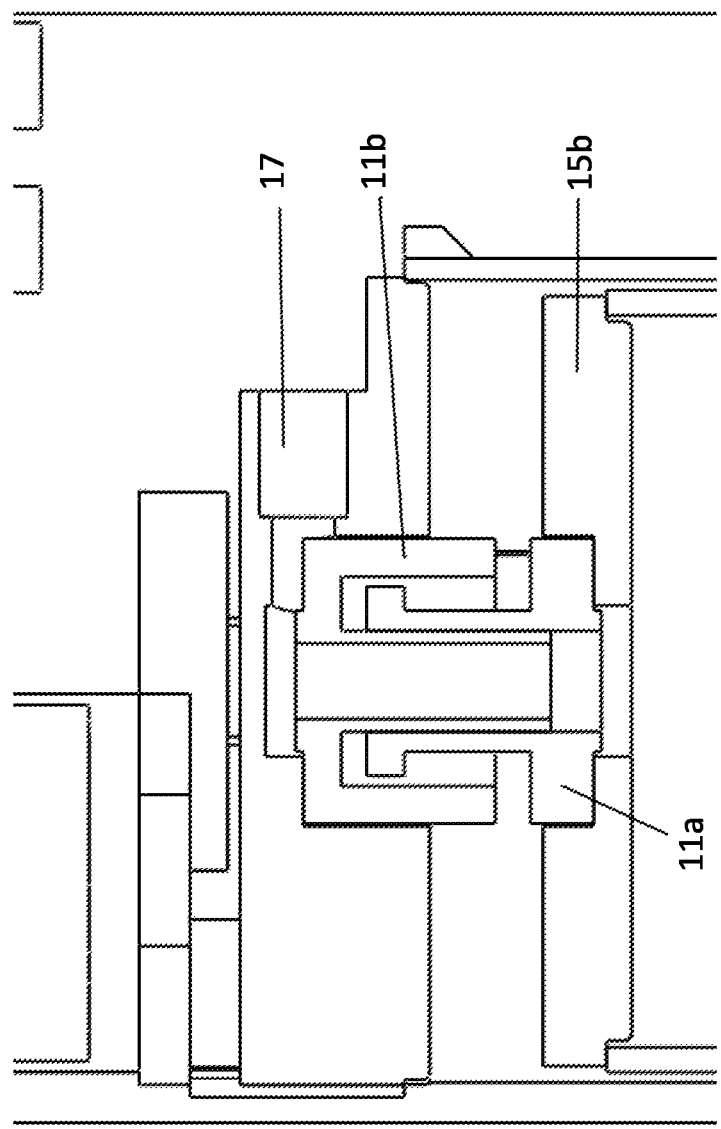
FIG. 7 shows a cross-sectional view of the controller box with the reservoir/container inserted and the luer lock section expanded.

As shown in FIG. 6, one is able to generate negative or positive pressure in the controller box 1 by use of a pump 13 that causes the piston 30 to move either in a direction towards the luer lock 11 or towards the nozzle/conduit 8, respectively. When the piston moves in a direction towards the luer lock 11 meaning there is a negative pressure (relative to the atmospheric pressure) present in the controller box 1, one is able to draw in liquid (fluid) or air because the piston moves in a direction towards the luer lock 11 using aspiration. This would allow one to clean a wound (e.g., remove liquid from it). When the pump generates a positive pressure in the controller box (relative to atmospheric pressure), the piston 30 moves in the opposite direction and air (or fluid) is expelled from the container/reservoir 10 allowing one to irrigate a wound, nasal passage, or ear canal.

As an example, the device/apparatus may be part of a kit that contains sterile water (or saline), which may have antibiotics or other useful compounds in it. An operator of the device would turn the suction/ejection switch 9 (FIG. 3) to suction, place the nozzle/conduit 8 of the container/reservoir 10 into the sterile water and depress the pump-on switch 2 (FIGS. 1 and 2), thereby generating a vacuum in the controller box 1, which in turn moves the piston 30 in a direction towards the luer lock 11, thereby allowing the sterile water to be drawn into the inside of the container/reservoir 10. Turning the suction/ejection switch 9 to the eject and depressing the pump-on switch 2 would then move the piston in the opposite direction (i.e., towards the nozzle/conduit 8) thereby ejecting the sterile water, for example, into a wound. One could then again turn the suction/ejection switch 9 to suction, place the nozzle/conduit 8 of the container/reservoir 10 into the water, which is in the wound, and depress the pump on switch 2, thereby again generating a vacuum in the controller box 1, which in turn moves the piston 30 in a direction towards the luer lock 11, thereby allowing the water from the wound to be drawn into the inside of the container/reservoir 10. Again, turning the suction/ejection switch 9 to the eject and depressing the pump on switch 2 would then move the piston in the opposite direction (i.e., towards the nozzle/conduit 8) thereby ejecting the water that had cleaned the wound into a disposal container. This process can be repeated several times allowing one to effectively clean a wound.

The device may come as part of a kit wherein the kit would at a minimum contain the controller box and the container/reservoir. The kit might also contain a carrying case for the device, the various attachments (discussed below) that can be used to clean ears, nasal passages, and wounds, batteries, electronics that can be easily replaced, and vials that contain sterile water, or saline with antibiotics, hydrogen peroxide, various mineral oils and other things. The kit may also contain additional containers/reservoirs and a repository for the used containers/reservoirs that allows them to be disposed of or alternatively saved so that they can all be washed together at a later time. The kit may contain any of the things that are mentioned herein.

In an embodiment, there are a number of attachments that can be attached to the nozzle/conduit 8, such as the attachments that are shown as silicon nozzles or catheters 19, 20, 21, 25 (FIGS. 10, 11, 12, and 13). In an embodiment, the syringe-like reservoir/container 10 could be disposed and replaced with sterile or non-sterile reservoir/container should the operator elect to replace rather than clean and/or disinfect. In an embodiment, the reservoir/container 10 might have gradations associated with and present on it so that a user will know the volume of liquid that is being drawn into or expelled from the reservoir/container 10. The controller box 1 might have one or more slits 6 (FIGS. 1 and 2) associated with it that allows a user to see the gradations on the reservoir/container 10 when it is present in the controller box, thus allowing one see these gradations to ascertain the amount of fluid present in the reservoir/container 10 without removing the reservoir/container 10 from the controller box 1. In an embodiment, the disposable syringe reservoir/container 10 is housed in a sealed compartment 15 (sealed compartment 15 is defined by cylinder wall 15*a* and the end cap/syringe cover 15*b*) in the device to prevent contamination of the remainder of the device. The sealed compartment 15 in an embodiment may have a cylinder wall 15*a* and an end cap/syringe cover 15*b* associated with it (see FIGS. 5 and 6). The cylinder wall 15*a* and the end cap/syringe cover 15*b* serve the purpose of keeping the reservoir/container 10 separate from the rest of the controller box 1 and also provide the reservoir/container 10 with a good fit in the compartment in the controller box 1 that is to contain the reservoir/container 10.

In one embodiment, the device may be operated by powerful rechargeable batteries 14 (FIG. 6) that have a power level indicator board 4 (FIG. 2) and are controlled by a motor speed control module with display 5 (FIG. 2) that is connected to an on/off power switch 31 (see FIG. 4). The power level indicator board 4, in one embodiment may have a single light associated with it that changes color as the power in the battery is drained. For example, the light may be green when fully charged and it may go through the colors, yellow, orange to red as the battery is drained. Alternatively, but not shown, there may be a plurality of lights associated with the power level indicator board 4 wherein all of the lights are illuminated when fully charged and as the battery drains, the number of lights that are illuminated decreases. When only one light is illuminated, the operator may prudently opt to recharge the batteries associated with the controller box.

In one embodiment, there is also a pump-on switch 2 that activates the pump (FIGS. 1 and 2). The on/off power switch 31 (FIG. 4) when in the on position turns power on to the pump but the pump remains in stand-by mode. Depressing the pump-on switch 2 (FIG. 2) will activate the pump so that it is either evacuating air from the controller box thereby creating negative pressure relative to atmospheric pressure or alternatively creating positive pressure in the controller box relative to atmospheric pressure thus expelling air out of the container/reservoir. The amount of power that goes to the pump is controlled by an adjustable knob 3 (FIG. 2) that controls the motor speed control module 5 (FIG. 2) thereby allowing more rapid or slower generation of positive and negative pressures in the controller box 1.

In one embodiment, the rechargeable batteries 14 (FIGS. 6 and 9) may be recharged by AC power connected to a charging connector plug 12 (see FIG. 4) (e.g., plugging the batteries into a wall outlet). Alternatively, the controller box 1 may have solar panels associated with it that allows the rechargeable batteries to be recharged by light (not shown in a figure). This last embodiment would allow the device to be useful in situations where electricity might not be readily available, for example by medics in a war zone, or out in the "bush", or potentially in a rural area of a developing country that might not readily have electricity available. It is also contemplated that the device may also work by directly plugging the device into a wall outlet (using an AC power source), or by using disposable batteries (e.g., using a disposable DC source of power).

The device of the present invention has the functions to be used as mini ultraportable digitally adjustable wet/dry vacuum and irrigator with a plurality of combined applications in both outpatient and in-home settings. In one embodiment, the device may be comprised using off the shelf components. In one embodiment, smaller components can be special ordered or made to ordered to make the device smaller than the size described herein. Also, it is contemplated that the size of the device may alternatively be made so that is bigger than described herein. The device will have universal applications including, but not limited to, wound aspiration, wound lavage, nasal aspiration, nasal lavage, cerumen removal, and cerumen lavage. The wide use of this device will minimize the economic impact of patient's sick time and possibly contribute to a safer/greener environment by reducing the use of facial disposable tissues, gauze, and compresses and other disposable medical cloth like materials.

When sterile conduit/catheter and/or sterile needle and/or sterile disposable reservoir/container are used, additional applications include aspiration of infected and non-infected body fluids, cavities, closed and open wounds. An ideal example of the use of this device in such settings would be aspiration of pustular contents of incised abscesses, suctioning and drainage of infected wounds, aspiration of minor bleeding, irrigation of wounds, aspiration of synovial fluid/intraarticular fluids and other similar medical procedures.

Figure 8:
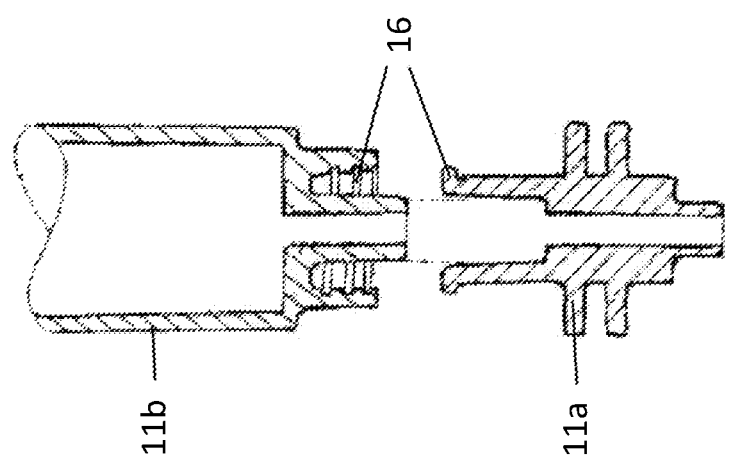
FIG. 8 shows a cross-sectional view of an embodiment of the luer lock that allows connection of the controller box to the reservoir/container.
Figure 9:
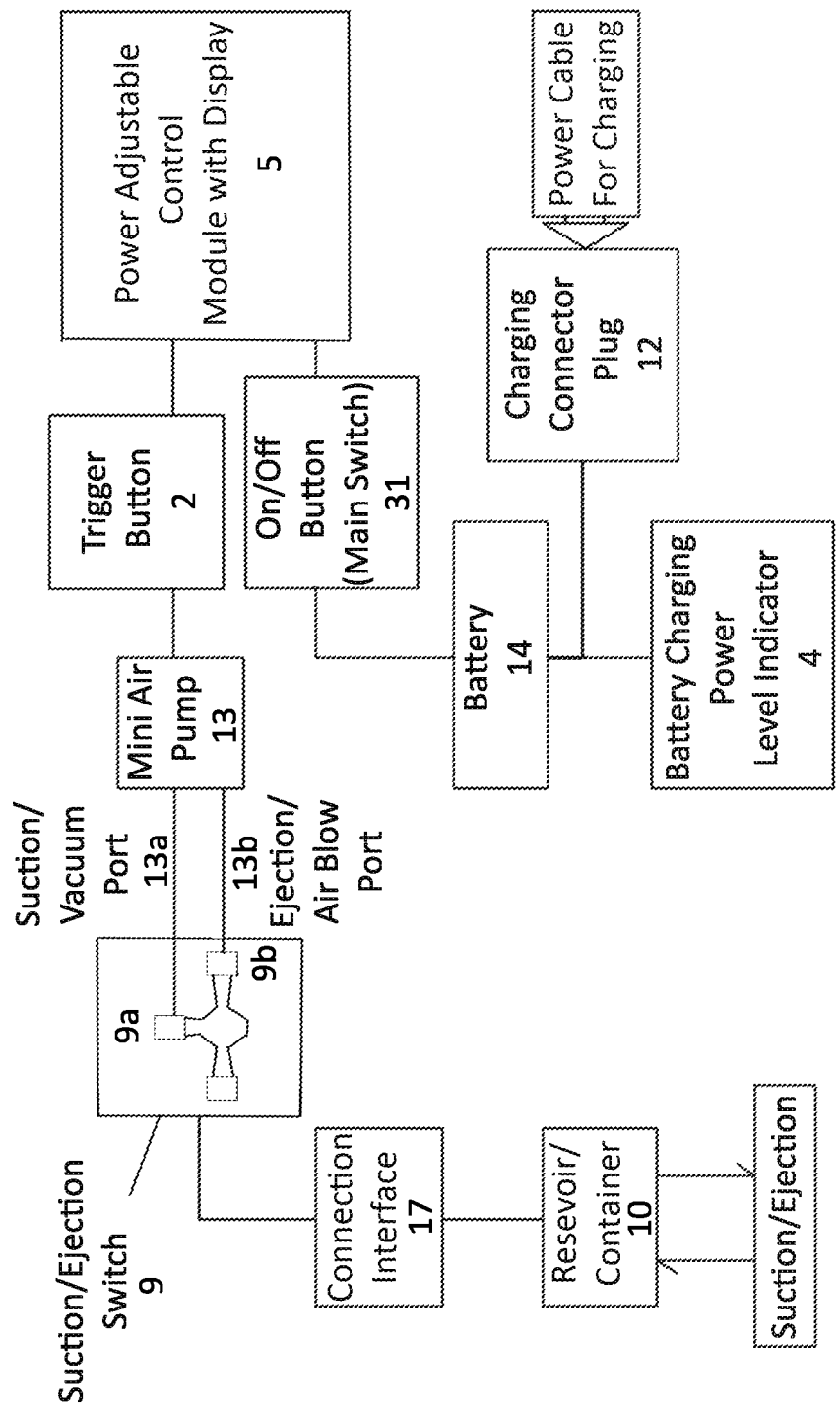
FIG. 9 shows a schematic as to how the various power components of the controller box are related.

In an embodiment, and as shown in FIG. 9, the controller box 1 houses rechargeable lithium ion or lead acid batteries 14 that are connected to a charging connector plug 12, to a battery charging power level indicator board 4 and to a power adjustable control module [Printed Circuit Board Assembly (PCBA)] with display 5. In one embodiment, the device can be manufactured using off the shelf components. A mini air pump 13 is operationally connected to the reservoir/container 10 and is controlled by a power adjustable control module 5 that modifies the pump's suction and or ejection power. The pump 13 has a suction/vacuum port 13*a* and an ejection/air blow port 13*b* associated with it. The mini air pump ports 13*a* and 13*b* are attached to a manual suction/ejection switch 9. Although the suction/ejection switch 9 is shown as a manual/mechanical switch that involves the user moving a lever to toggle back and forth between suction and ejection, it should be understood that in a variation, the switch may be any of a plurality of designs such as a button that allows one to depress the button and toggle between suction and ejection or other means of toggling between these actions that are known to those of skill in the art. In the embodiment shown, suction/ejection switch 9 has a suction port 9*a* that activates the suction/vacuum port 13*a* and ejection/air blow port 9*b* that activates the ejection/air blow port 13*b*. The suction/ejection manual switch 9, in one embodiment, is operationally attached to a disposable/replaceable syringe reservoir/container 10. As shown in FIGS. 2 and 3, one end 7 of the disposable/replaceable syringe reservoir/container 10 is exposed and protruding out of the controller box 1 and has protruding knobs 18 (FIG. 1) on the outer circumference to assist in twisting and replacing the syringe-like reservoir/container 10. The end 7 (FIGS. 1 and 2) also has associated with it a nozzle 8 to which a conduit could be fitted (note the nasal, ear, and wound conduits 19, 20, 21, 25, 26, 37, 38, 39, and 40) In an embodiment, the syringe-like reservoir/container 10 may be inserted into the controller box 1 wherein when reservoir/container 10 is completely inserted into the controller box 1, there may optionally be associated with the controller box a flap 32 attached to controller box 1 by a hinge 33 (see FIGS. 1 and 2). The hinge 33 may be a flexible part of controller box 1 or a joint or joints attached to the controller box 1. The flap 32 may be dome like, circular, rectangular or any other shape that is the same shape as the circumference of reservoir/container 10, and the flap 32 has a central or peripheral hole 34 (FIGS. 2 and 3) that allows for nozzle 8 to protrude through it when the reservoir/container 10 is completely inserted in controller box 1. In an embodiment, the flap 32 latches to the controller box 1 to stabilize and support the syringe-like reservoir/container 10 and minimizes stress on luer lock 11 (see FIGS. 6, 7, and 8), especially when syringe-like reservoir/container 10 is filled with fluid and controller box 1 is inverted. The other end of the disposable reservoir/container 10 has a luer lock 11 by which it is locked into the machine-syringe interface mount 17. This luer lock 11, in one embodiment, is composed of female luer lock 11a that fits into a male luer lock 11b. It should be understood that the female and male luer lock 11a and 11b may be present in either direction. That is, the male luer lock 11b may be associated with either the reservoir/container 10 or the interface mount 17 as long as the other one (the interface mount 17 or the reservoir container 10) has the corresponding attachable female part. The male luer lock 11b is partially tapered at its tip where it fits into the female luer lock 11a to pierce and allow operational connection of the capped prefilled or sterile syringe-like reservoir/container 10. A thread lock 16 may be present that tightens the seal between the female luer lock 11a and the male luer lock 11b that prevents any fluid leak. The disposable/replaceable syringe reservoir/container 10 fits into a compartment 15 which is sealed from other components of the device by thin cylinder like partition plate cylinder wall 15a (FIG. 5) and end cap/syringe cover 15b (see FIGS. 6 and 7). The controller box 1 in one embodiment, has a clear slot 6 associated with the controller box 1 that allows a user to observe the fluid/volume level inside the disposable/replaceable syringe reservoir/container 10. In one embodiment and as shown, the machine-syringe interface mount 17 houses the luer lock male 11b component, as well as the threaded lock 16 (FIG. 8).

In one embodiment, nasal conduits 19 (FIG. 10) may be used that are made of soft silicon and vary in size and shape (note nasal conduits 19a, 19b, and 19c) to fit the appropriate nostril size and provide optimal comfort. Nasal conduits 19a and 19b, in an embodiment, can be used for the aspiration of the nose and these conduits have one channel to which the device's nozzle 8 connects. There may also be a conduit for nose lavage/irrigation 19c, which has one channel for irrigation 19c1 to 19c2 to which the device's nozzle 8 connects and a second channel 19c3 to 19c4 for irrigant outflow that can be drained into a collecting basin 24 (see FIG. 12, wherein the collecting basin can be also be used for an ear conduit).

In an embodiment, a bi-nostril conduit 26 (FIG. 14) may be attached to the reservoir/container 10 and may be principally used for aspiration and comprised of Y-shaped plastic tubing ends 28 made of soft corrugated plastic 26a that allows for adjustment for ideal use and comfort. The bi-nostril conduit's tubing 26b is similar to conduit 26a except that the end part 27 in one embodiment is made of a more rigid non corrugated plastic and connects to the nozzle/conduit 8. Two soft silicon buds 19a, 19b, or similar buds can be fitted to the ends of the Y-shaped plastic tubing 28.

Ear conduits 20 (FIG. 11) and 21 (FIG. 12) also vary in size and are designed to fit into the ear's 22 external auditory canal 23. Conduit 20, in an embodiment is a conduit that can be used for aspiration of the external auditory canal 23 and has one channel to which the device's nozzle connects. The conduit for ear lavage/irrigation 21 has one channel for irrigation 21a and 21b to which the device's nozzle connects and a second curved channel 21c and 21d for irrigant outflow to pour into a collecting basin 24.

Figure 13:
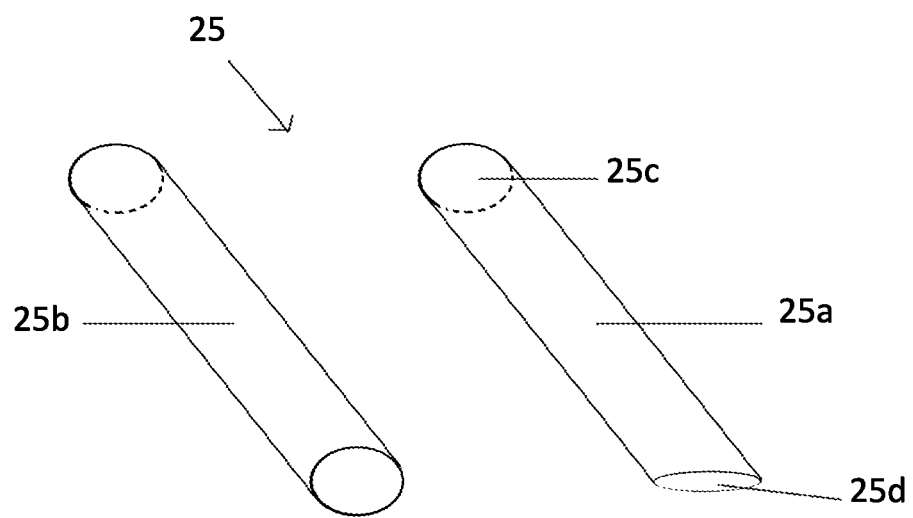
FIG. 13 shows cross sectional embodiments of wound conduits.

In an embodiment, conduits for open wound therapy 25a and 25b have one channel and vary in size and could be rounded in shape 25b or alternatively, may be oval 25a in shape (see FIG. 13). Conduit 25a has a rounded end 25c to fit nozzle 8 and flat/oval end 25d for wound irrigation/aspiration. The shape of the conduit will be appropriately selected by the user based upon need.

Figure 17:
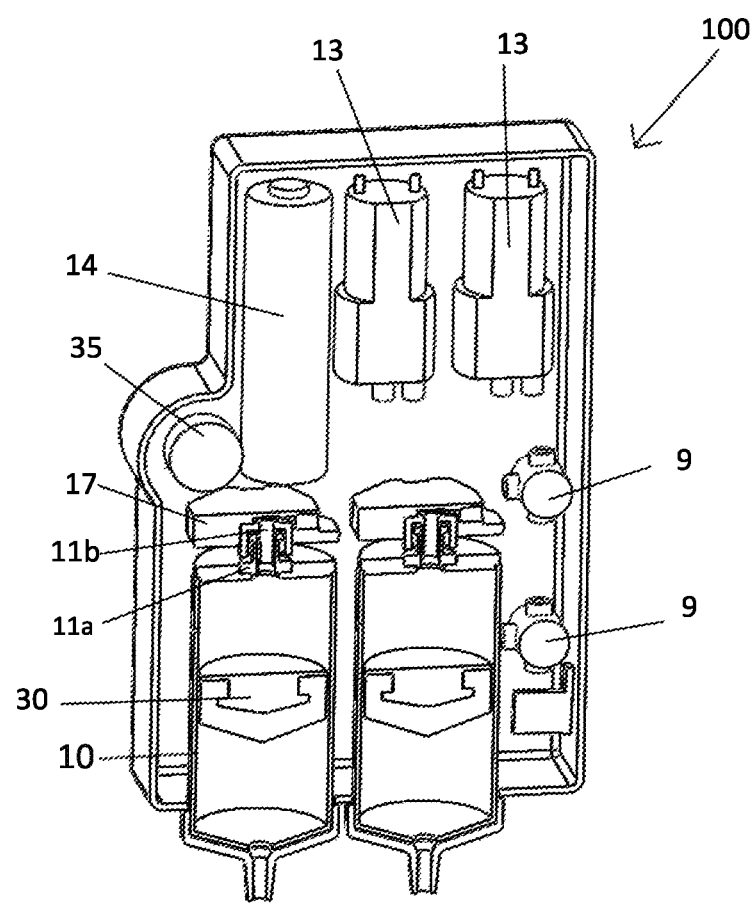
FIG. 17 shows a cross-sectional view of a device that has two container/reservoirs present in the controller box.
Figure 18:
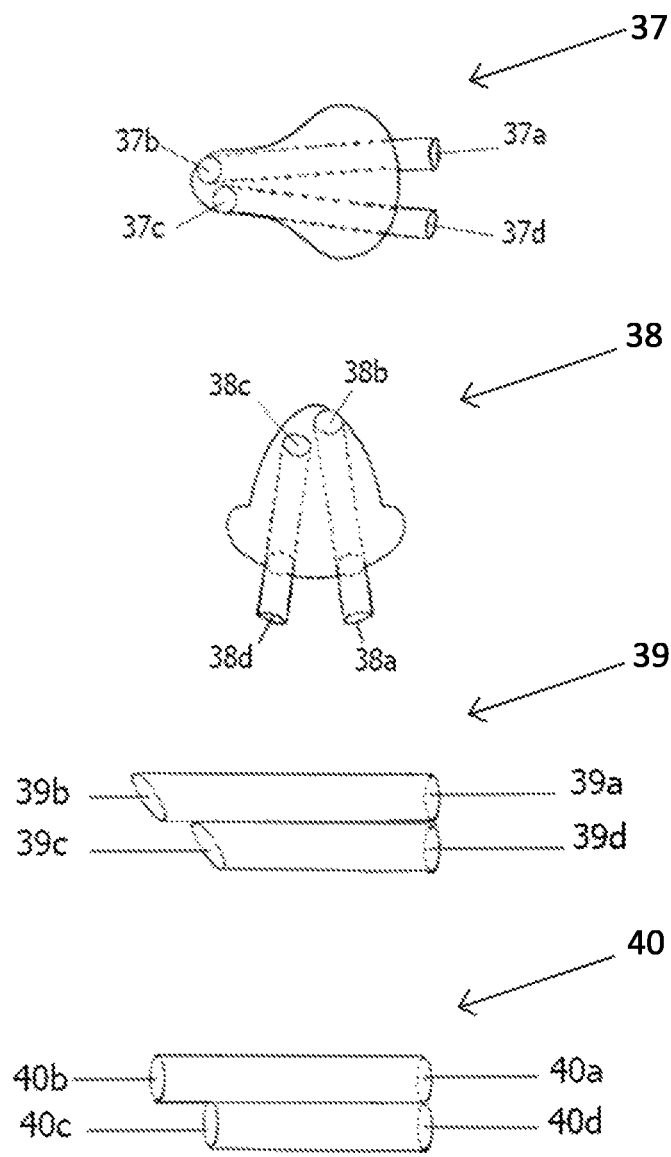
FIG. 18 shows perspective and cross-sectional views of conduits that are designed for the ear 37, nose, 38, and for wounds 39 and 40.

FIG. 18 shows additional conduits 37, 38, 39, and 40 that can be used for the ear 37, the nose 38, and for wounds 39 and 40. It is contemplated that in one embodiment these conduits are made out of silicon or some other soft plastic such as flexible PVC, clear silicon, or a mix of silicone and polysulfone that provides ideal comfort to the user. As shown, ear conduit 37 may have two passageways 37a-37b and 37c-37d that allows fluids and/or air a passageway of ingress and egress to and from the ear. Similarly, nose conduit 38 may have two passageways 38a-38b and 38c-38d that allows fluids and/or air a passageway of ingress and egress to and from a nostril. It should be understood that two separate nose conduits 38 may be used so that a patient may have both nostrils lavaged/aspirated at the same time. The wound conduits 39 and 40 that are shown rely on the same principal that two separate passageways in each of the wound conduits 39a-39b and 39c-39d in wound conduit 39 as well as 40a-40b and 40c-40d in wound conduit 40 allow for sequential or simultaneous lavage and aspiration of wounds. Wound conduit 39 has rounded ends 39a and 39d to allow attachment to two nozzle 8 and flat/oval ends 39b and 39c for wound aspiration/irrigation. Wound conduit 40 has rounded ends 40a and 40d to allow attachment to two nozzle 8 and flat/oval ends 40b and 40c for wound, aspiration/irrigation. In an embodiment, and as shown, passageway 39c-39d is shorter in length than passageway 39a-39b in wound conduit 39 and passageway 40c-40d is shorter in length than passageway 40a-40b in conduit 40 to minimize immediate aspiration of fluid and/or air ejected by the longer length passageways 39a-39b in conduit 39 and 40a-40b in conduit 40. The simultaneous processes can be easily achieved with the controller box 100 that contains at least two containers/reservoirs 10, with each container/reservoir performing the simultaneous functions of suction and aspiration, respectively. See FIGS. 15-17.

Figure 19:
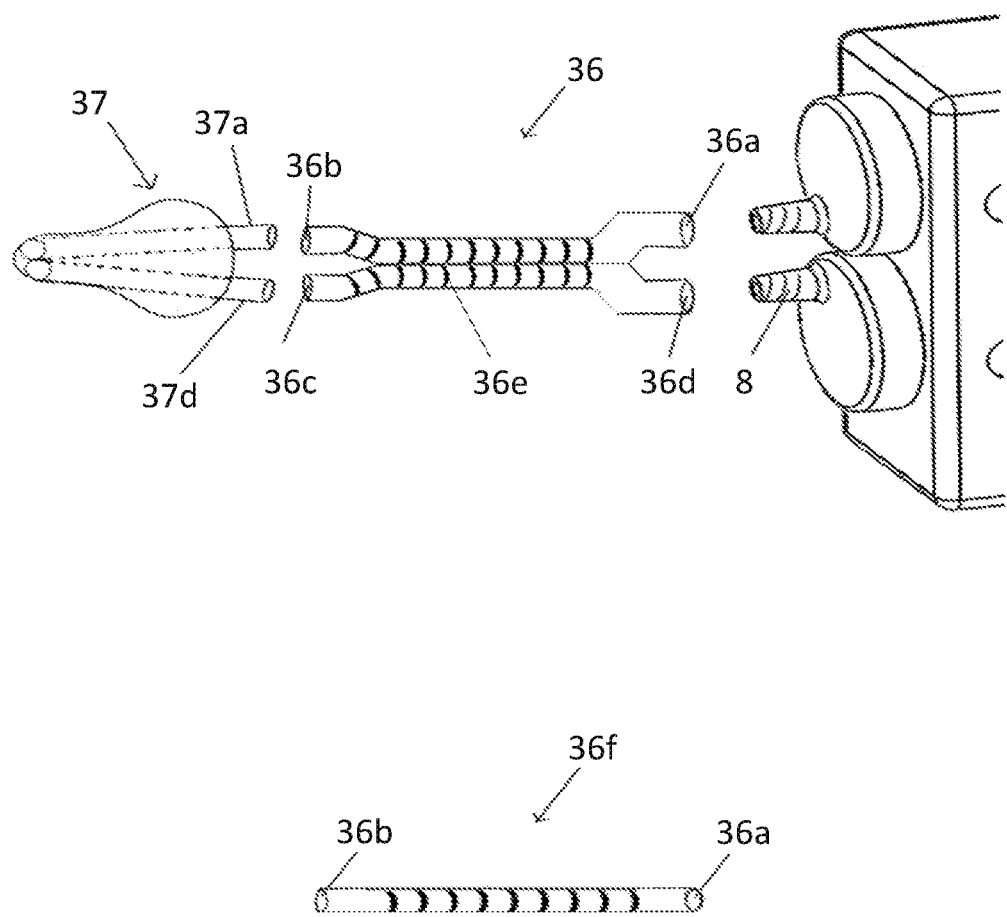
FIG. 19 shows a perspective view of how a conduit for the ear 37 may be attached to the nozzles/conduits 8 of the containers/reservoirs through connector 36.

FIG. 19 shows a perspective view of how the ear conduit 37 might be attached to the nozzles/conduits 8 through connector 36. It should be noted that the controller box 100 contains two containers/reservoirs 10 in this embodiment meaning that there are two nozzles/conduits available to attach to connector 36. It should be noted that connector 36 has two passageways 36a-36b and 36c-36d that allows the passage of fluid and/or air in either direction. This allows for either simultaneous or sequential ejection and aspiration of fluids and/or air. As is shown in FIG. 19, the connector 36 may have corrugated plastic 36e associated with the connector 36 that provides flexibility to the connector 36 allowing extension and compression of the connector 36 as well as the possibility of bending the corrugated plastic 36e. Although the connector is shown as being of a length that is on the order of size of the ear conduit 37, it should be understood that a much longer connector 36 is contemplated that would allow for a much greater distance between a patient and a person operating the controller box thereby providing safety (due to distance between them) to each of the individuals. In another embodiment, connector 36f (FIG. 19) has one passageway 36a-36b that allows the passage of fluid and/or air in either direction and to be used with conduits 19, 20, 21, and 25 attached to one end and nozzle 8 of controller box 1 attached to the other end. Also, it is contemplated that a harder plastic may be used for the connector 36 that would provide some rigidity and stability that may not be attained when softer plastics are used.

Figure 20:
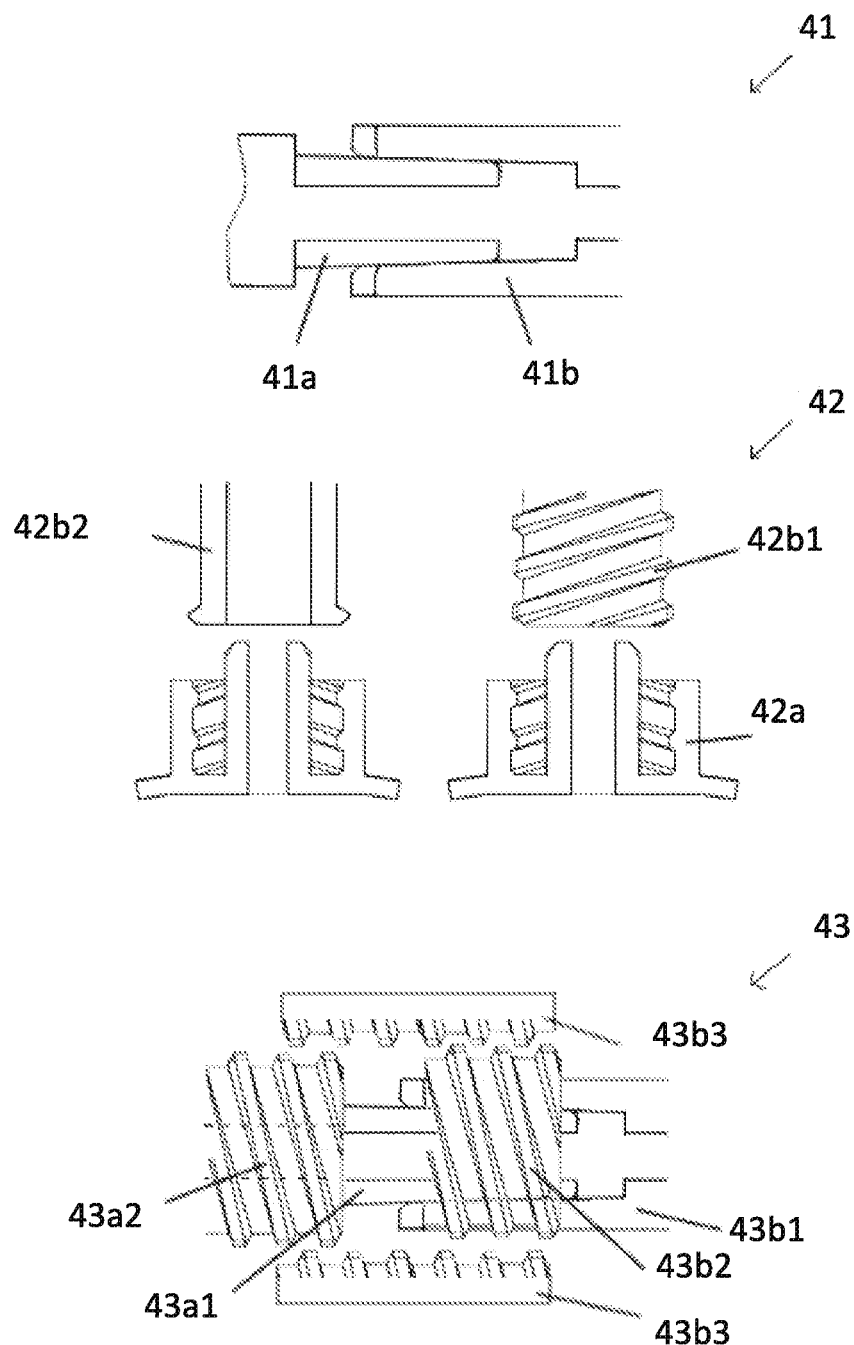
FIG. 20 shows various cross-sectional views of a plurality of different embodiment combinations that can be used in the present invention to attach two or more of the following components of the device: 1) one or two nozzles 8, 2) the conduits (any of 19, 20, 21, 25, 26, 37, 38, 39, and 40), and/or 3) connector (whether 36 or 36f).

FIG. 20 shows several cross-sectional views of embodiments that can be used as variations of the locks connecting between two or more of the following components of the device: 1) one or more nozzles 8, 2) the conduits (any of 19, 20, 21, 25, 26, 37, 38, 39, and 40), and/or 3) connector (36 or 36f). Luer lock 41 is shown as a conical luer lock that has a male connector fitting 41a and in this embodiment, a 6% taper to its sides. The corresponding female connector fitting 41b is ideally adapted to fit, attach, and secure the male connector fitting 41a to it, providing a tight connection between the two fittings.

In FIG. 20, Skirt and lug luer lock 42 shows a cross sectional view 42b2 and a front view 42b1 of the female connection fittings. The cross sectional view shows how male connection fitting 42 a would be able to be inserted into female connection fitting 42b. Female connection fitting 42b1 has threads associated with it that allows it to be screwed into the corresponding threads that are present on male connection fitting 42a thereby providing a screw tight fit of the female 42b1 and male connection fitting 42a.

FIG. 20 also shows side view with partial cross sectional view of a retractable/sliding luer lock skirt 43. This embodiment comprises a threaded female luer connector 43b1 with threaded collar 43b2 and threaded sleeve 43b3. Part of the threaded sleeve slides over male connector 43a1 with threaded collar 43a2 to which the sleeve of female connector 43b3 slides over to lock the luer lock in place, thereby providing a secure and tight fitting.

In an embodiment, the present invention may have potential antibacterial agents that can be integrated into other fluids such as the sterilized water that may be used in the device of the present invention. Included are the known chemical antibiotics that are typically used as well as other natural products, that are known to have antibacterial properties such as essential oils. Some of the most commonly used essential oils against multidrug-resistant microorganisms, such as tea tree, St. John's Wort, lavender and oregano are contemplated as potential substances that may be added to the sterilized water or other fluids of the present invention. Other compounds such as silver, gold, and zinc nanoparticles alone or functionalized with diverse antimicrobial compounds may be added to the sterilized water or other fluids to aid in the treatment of a human that has had foreign matter/organisms introduced into that human's person.

Although the present device has been described with reference to there being only one container/reservoir present in the controller box at one time, it is contemplated and therefore within the scope of the invention that the controller box 100 may contain at least two containers/reservoirs that can both be inserted in the controller box at one time. In this embodiment, it is contemplated that there will be a partition that exists in the controller box 100 that keeps the two containers/reservoirs separate from each other. Each of the containers/reservoirs would be operationally connected to their own pump (meaning the controller box 100 contains at least two pumps). This would allow a user to use one of the containers/reservoirs for ejecting fluid/air while the other container/reservoir could be used or dedicated to the aspiration of air/fluid. This would allow a user to, for example, draw 30 mls of fluid into one of the containers/reservoirs and continuously or intermittently eject this fluid in multiple 5-10 mls aliquots, while simultaneously (when two containers/reservoirs 10 in one controller box 100 are used) or sequentially using the other container/reservoir to withdraw these aliquots of fluid (which may have been used, for example, to clean a wound). An additional selector switch might be present on the controller box 100 that allowed one to select which pump to activate and consequently, which container/reservoir to use to alternatively eject or aspirate fluid.

With the above description, it should be apparent that the present apparatus has several advantages that are not present in the devices in the prior art. These advantages include the ability to use disposable containers/reservoirs thereby reducing the amount of cleaning needed. Another advantage of the present invention is that the syringe like containers/reservoirs do not have a rod in them (like typical syringes that move the piston) that might potentially contaminate the containers/reservoirs. An additional and significant feature of the present invention is that it operates in any position including in an inverted position. One feature that confidently provides a user the ability to use the device in the inverted position is the flap 32 that provides additional security beyond the luer lock 11, which securely positions the container(s)/reservoir(s) 10 in the controller box 1 and 100. This is superior to the devices of the prior art that can really only function in an upright position.

The devices of the prior art also rely heavily on one-way, two-way and three-way valves that are potential places for failure. Because the present invention does not have this valves, the apparatus of the present invention is simpler but at the same time more elegant, and perhaps more importantly, less likely to fail due to faulty valves. The device of the present invention in one embodiment also has the advantage that it is small enough (will fit in a person's pocket) to be easily portable but at the same time able to handle sufficient volumes (up to 50 mls) in inverted as well as upright positions so as to be useful for the purposes described herein.

Figure 15:
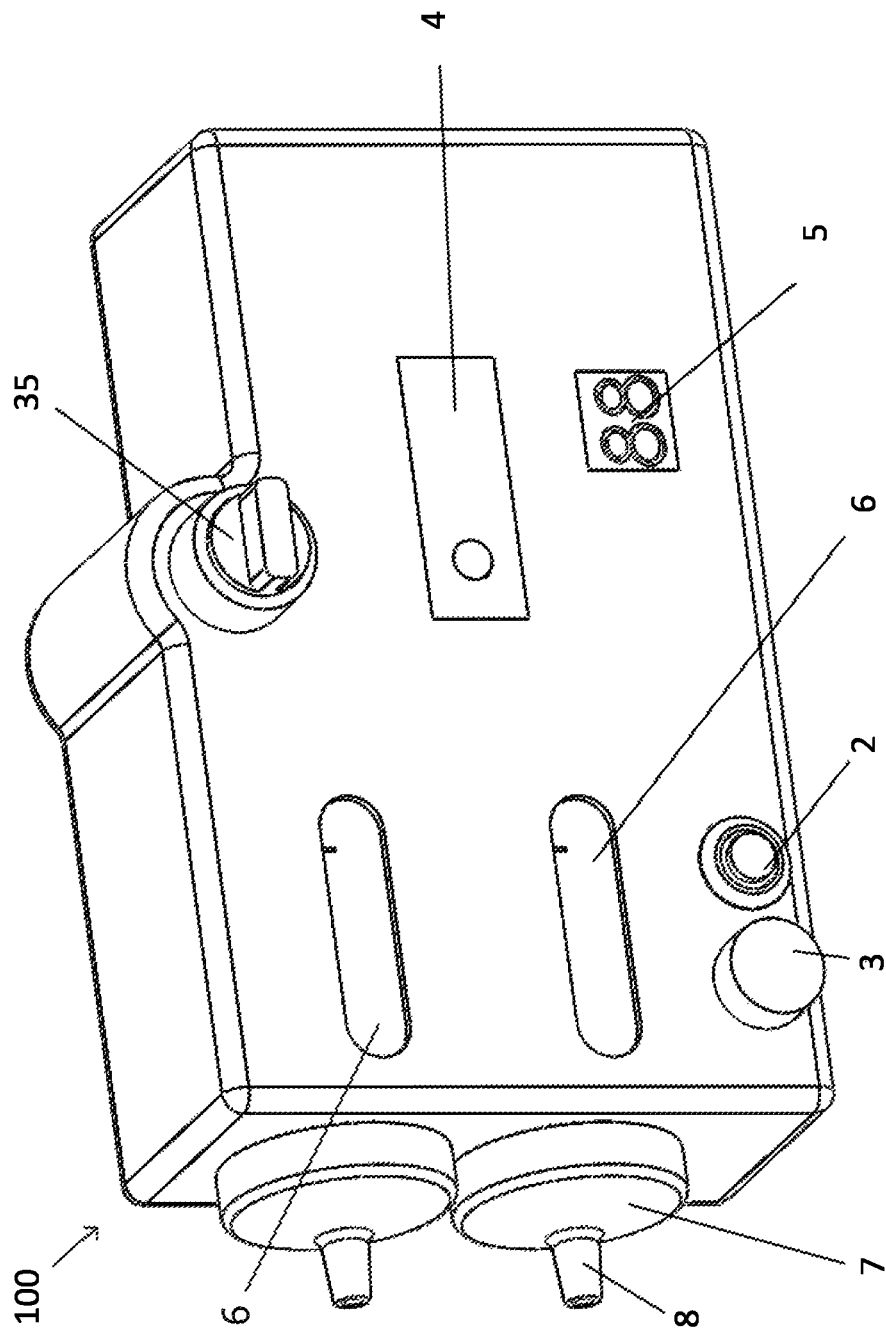
FIG. 15 shows a perspective view of a device that has two container/reservoirs present in the controller box.
Figure 16:
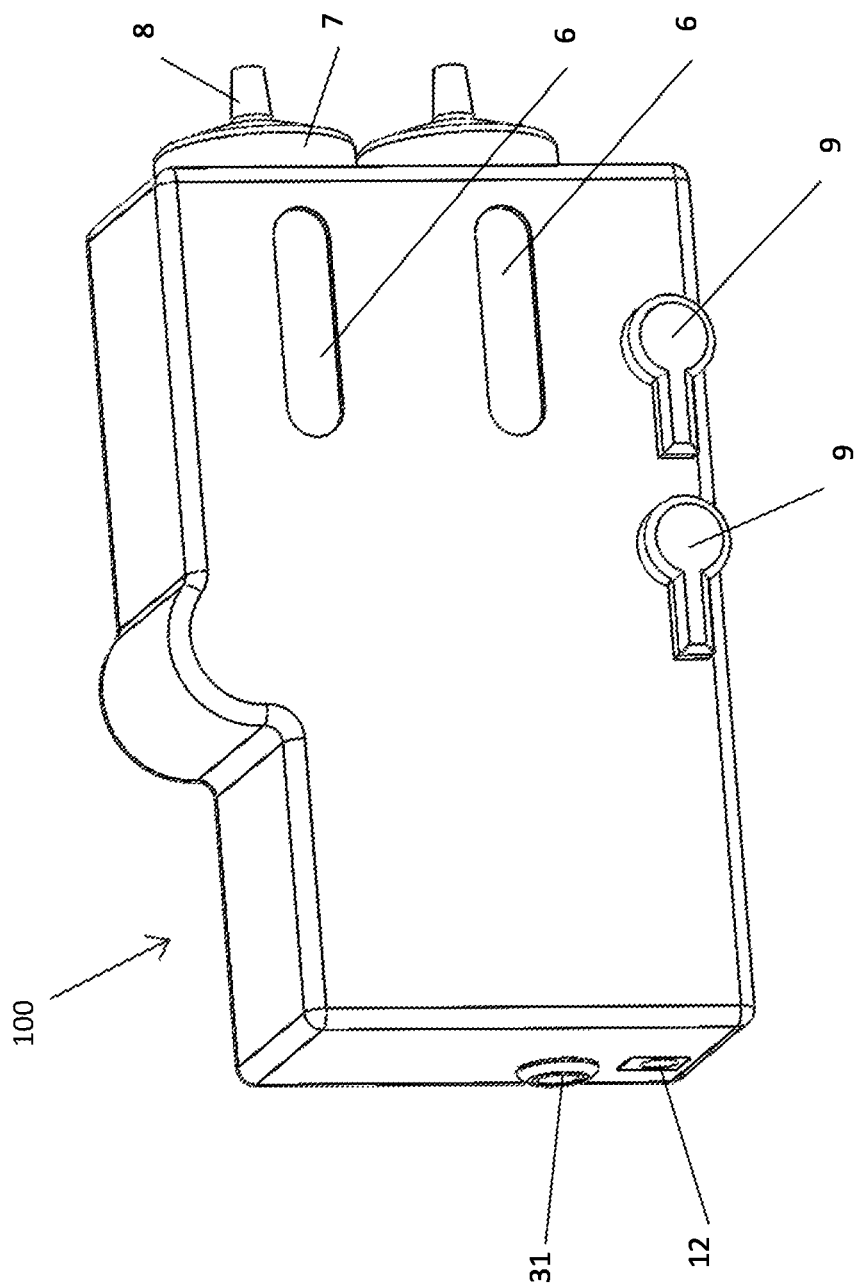
FIG. 16 shows another perspective view of a device that has two container/reservoirs present in the controller box.

In an embodiment and as shown in FIGS. 15-17, the device of the present invention may contain a controller box 100, with two or more container/reservoirs 10. In one variation of the purpose, this would allow a user to that is using a controller box 100 that has at least two container/reservoirs to use the first container/reservoir exclusively for irrigation and the second container/reservoir exclusively for aspiration to achieve simultaneous or near simultaneous irrigation and aspiration. It also allows a user to squirt (irrigate or eject) only a part of a fluid that is contained in the first container/reservoir into the orifice to be treated and the second container/reservoir can be used to suck in (aspirate)

the liquid which has been squirted into the orifice. Subsequently, more fluid from the first container/reservoir (a second batch) can be used to irrigate the orifice and the second container/reservoir can then aspirate this second batch of fluid from the orifice. This process can be continued until the first container/reservoir has no more fluid in it or until the second container/reservoir sis full.

In an embodiment, the controller box that is able to house two containers/reservoirs may have at least two separate pumps, with a first pump being operationally attached to the first container/reservoir and the second pump being operationally attached to the second container/reservoir. The device may also have one or two separate suction/ejection switches 9, one or two batteries 14, one or two power level indicators 4, one or two motor speed control modules with one or two displays 5. The controller box 100 would have the appropriate switch(es) 35 on it that allows for a user to control either the first pump, the second pump, or both simultaneously (sometimes in unison) depending on what the user wanted to do. For example, in one embodiment, a switch 35 might be present that has a number of different settings. The first setting might control the first pump and the corresponding first container/reservoir, the second setting might control the second pump and the corresponding second container/reservoir, a third setting may allow the first pump to work in unison, and a fourth setting may allow the pumps to work at the same time with opposite effect, meaning that the first and the second container/reservoir may work together in unison or alternatively, to allow for simultaneous irrigation and aspiration.

In an embodiment, the size of the controller box that is designed to house two containers/reservoirs might have a size that is on the order of 95 mm×45 mm×172 mm. It should be understood that other sizes are contemplated for this controller box. The kit that may have this controller box in it might also contain a controller box that is designed to house a single container/reservoir. The kit may have an adaptable carrying case that can be adjusted so that it can carry the controller box that is designed to house either one or two containers/reservoirs.

The other features present on the controller box 1 that is designed to house a single container/reservoir 10 would also be present on the controller box that is designed to house a plurality of containers/reservoirs with the appropriate modifications made for the multiple containers/reservoirs. For example, the controller box that is designed to house a plurality of containers/reservoirs would have two or more transparent slits 6, so that each of the containers/reservoirs can be viewed by the user. However, the electronics would also be appropriately adapted for the plurality of containers/reservoirs.

In an embodiment, the present invention relates to an apparatus that comprises: a controller box and a container/reservoir designed to fit snugly in the controller box, the controller box comprising a pump that is configured and designed to create a positive or negative pressure in the controller box thereby moving a piston present in the container/reservoir when the container/reservoir is present in the controller box, wherein the movement of the piston allows aspiration and/or irrigation of fluids and/or gas by the movement of the piston.

In an embodiment, the apparatus further comprises one or more of a suction/ejection switch, a nozzle/conduit, a luer lock, a motor speed control module, batteries, a slot, an on/off power switch, a pump-on switch, a gasket, a solar panel and a power connector plug. In a variation, the apparatus comprises all of the suction/ejection switch, the nozzle/conduit, the luer lock, the motor speed control module, the batteries, the slot, the on/off power switch, and the power connector plug. In a variation, the batteries comprise lead acid or lithium ion batteries. In an embodiment, the batteries are charged by solar power or by AC electricity.

In an embodiment, the container/reservoir is cylindrical in shape and the container/reservoir comprises gradations on the container/reservoir allowing a user of the apparatus to see a volume of fluid present in the container/reservoir. In a variation, the container/reservoir comprises a nozzle/conduit that is configured to allow attaching attachments that can be used for cleaning ears, nasal passages, and wounds.

In an embodiment, the apparatus/device is part of a kit.

In a variation, the container/reservoir is of a size between 20 and 40 milliliters, or between 20-50 ml, or alternatively about 30 mls.

In a variation, the luer lock 11 is designed to engage and secure the container/reservoir 10 to the controller box 1 once the container/reservoir 10 is inserted into the controller box.

In a variation, the apparatus comprises a motor speed control module that controls a power of the pump either increasing or decreasing the ability of the pump to aspirate and/or irrigate the ears, nasal passages, and wounds.

In an embodiment, the attachments are designed to fit in ears, nasal passages, and/or wounds and comprise a soft plastic.

In an embodiment, the present invention relates to an apparatus for irrigating and aspirating ears, nasal passages, and wounds in a subject, said apparatus comprising a controller box and a container/reservoir, said container/reservoir being of a shape that is designed to fit snugly in the controller box, the container/reservoir having at least one open end and a luer lock associated with the container/reservoir that allows the container/reservoir to be engaged and secured to the controller box, the controller box comprising a pump that is designed to move a piston inside the container/reservoir, wherein the at least one open end is designed to allow passage of air and or fluids from an area that is outside the container/reservoir to an area inside of the container reservoir or from an area that is inside the container/reservoir to an area outside of the container reservoir.

In a variation, the apparatus further comprises one or more of a suction/ejection switch, a nozzle/conduit, a motor speed control module, batteries, a slot, an on/off power switch, a gasket, a solar panel and a power connector plug. In a variation, the suction/ejection switch is operationally connected to the pump so that when the suction/ejection switch is switched to a suction position the piston moves in a way that allows aspiration and when the suction/ejection switch is switched to an ejection position the piston moves in a way that allows irrigation.

In an embodiment, the motor speed control module controls a power of the pump either increasing or decreasing an ability of the pump to aspirate and/or irrigate the ears, nasal passages, and wounds.

In an embodiment, the present invention relates to a method of irrigating or aspirating ears, nasal passages, and/or wounds, said method comprising: procuring an apparatus that comprises a controller box and a container/reservoir, said container/reservoir being of a shape that is designed to fit snugly in the controller box, the container/reservoir having at least one open end and a luer lock associated with the container/reservoir that allows the container/reservoir to be engaged and secured to the controller box, the controller box comprising a pump that is designed to move a piston inside the container/reservoir, wherein the at least one open end is designed to allow passage of air and/or fluids from an area that is outside the container/reservoir to an area inside of the container reservoir or from an area that is inside the container/reservoir to an area outside of the container reservoir, wherein a user moves air and/or fluids from an area that is inside the container/reservoir to an area inside the ears, nasal passages, or wounds, and subsequently removing the air and/or fluids from inside the ears, nasal passages, and/or wounds, thereby irrigating and/or aspirating the ears, nasal passages, and/or wounds. In a variation the method further comprises applying antibiotics, baby oil, mineral oil, glycerin or hydrogen peroxide to the ears, nasal passages, and/or wounds using the apparatus.

In a variation, the method is performed over a plurality of times and usually, at least twice. In a variation, the method may be performed three, four or five, or more times. In a variation, the fluid in the apparatus may not be discarded until the method has been performed a plurality of times.

In an embodiment, the device of the present invention may have a controller box that has a plurality (usually two) containers/reservoirs associated with and housed in the controller box that allows the user great flexibility in the functions that can be attained by the device of the present invention. This flexibility allows the pumps to work either sequentially or simultaneously, and when the pumps work simultaneously, they may work either in unison (both irrigating or aspirating) or with separate effect (one pump irrigating while the other aspirates).

EXAMPLES

A working prototype of the present invention has been made and works as indicated herein. However, for pure illustrative purposes, the following example is a hypothetical example of how the device of the present invention might be employed.

A 22-year-old male patient with a 3-inch laceration would be treated with the device of the present invention. The device used would be the controller box 1 with a single container/reservoir 10. 30 ml of sterile saline solution would be first aspirated into the device by placing the pump in the aspiration mode by moving the switch to the suction mode and depressing the pump on switch, which would cause the sterile saline solution to enter the container/reservoir. The pump would then be placed in the irrigation mode by placing the switch in the ejection mode. The patient's laceration wound would be irrigated with the sterile saline by depressing the pump on switch. This process would be repeated several times. In this example, the pump would only operate when one continues to depress the pump on switch. That is, the pump will/would turn off when the user releases the pump on switch.

The controller box 1 and the container(s)/reservoir(s) 10 of the present invention would work in a similar manner if one were to irrigate/aspirate other orifices such as the nose or the ear of a patient.

It is contemplated that any of the features of the present invention that are described herein can be combined with any other feature that is described herein even if they are not described together (as long as they are compatible). When ranges are discussed every real number that is present in that range is contemplated as an end point for a subrange within that range. In any event, the invention is best defined by the below claims.

The following patents are incorporated by reference in their entireties for all purposes.

1. U.S. Pat. No. 6,991,638 B2 to Wang.
2. EP Patent No. 2 005 981 A2 to Chen et al.
3. U.S. Pat. No. 8,663,198 B2 to Baun et al.
4. U.S. Pat. No. 8,747,372 B1 to Schultz.
5. U.S. Pat. No. 4,206,756 to Grossan.
6. U.S. Pat. No. 8,048,023 B2 to Hoke et al.
7. U.S. Pat. No. 7,981,077 B2 to Hoke et al.
8. U.S. Pat. No. 8,801,667 B2 to Taylor et al.
9. US Patent Application Publication No. 20130046287 to Davis et al.

I claim:

1. An apparatus for irrigating and aspirating ears, nasal passages, and wounds in a subject that comprises:
   a controller box and one or more containers/reservoirs disposed almost entirely in the controller box,
   the controller box comprising one or more pumps that is/are configured and designed to create a positive pressure within the controller box and further configured to create a negative pressure in the controller box thereby moving one or more pistons present in the one or more containers/reservoirs,
   wherein movement of the one or more pistons causes aspiration and irrigation of fluids and/or gas by the movement of the one or more pistons,
   wherein irrigation and/or aspiration is/are prevented while the one or more pistons is/are stationary,
   said apparatus optionally having one or more conduits that can be operationally attached to the one or more containers/reservoirs thereby facilitating said aspiration and irrigation of fluids and/or gas through said one or more conduits.

2. The apparatus of claim 1, further comprising at least one of one or more suction/ejection switches, one or more nozzles/conduits, one or more luer locks, one or more motor speed control modules, one or more batteries, one or more slots, an on/off power switch, one or more pump-on switches, one or more gaskets, one or more solar panels, or a power connector plug.

3. The apparatus of claim 2, wherein the apparatus comprises the one or more suction/ejection switches, the one or more nozzles/conduits, the one or more luer locks, the one or more motor speed control modules, said one or more batteries, the one or more slots, the on/off power switch, and the power connector plug.

4. The apparatus of claim 3, wherein the one or more batteries are lead acid or lithium ion batteries.

5. The apparatus of claim 3, wherein the one or more containers/reservoirs are cylindrical in shape and the one or more containers/reservoirs comprise gradations on sides of the one or more containers/reservoirs allowing a user of the apparatus to see a volume of fluid present in the one or more containers/reservoirs.

6. The apparatus of claim 5, wherein the one or more containers/reservoirs comprise one or more nozzles/conduits that are configured to allow attaching attachments used for cleaning ears, nasal passages, and wounds.

7. The apparatus of claim 6, wherein the apparatus is part of a kit.

8. The apparatus of claim 1, wherein the one or more containers/reservoirs are of a size between 20 and 40 milliliters.

9. The apparatus of claim 3, comprising one or more luer locks, wherein the one or more luer locks are designed to engage and secure the one or more containers/reservoirs to the controller box once the one or more containers/reservoirs are inserted into the controller box.

10. The apparatus of claim 6, comprising one or more motor speed control modules, wherein the one or more motor speed control modules control power of the pump either increasing or decreasing an ability of the pump to aspirate and/or irrigate the ears, nasal passages, or wounds.

11. The apparatus of claim 10, wherein the batteries are recharged by solar power or by AC electricity.

12. The apparatus of claim 6, wherein the attachments are designed to fit in ears, nasal passages, and/or wounds and comprise a soft plastic.

13. An apparatus for irrigating and aspirating ears, nasal passages, and wounds in a subject, said apparatus comprising
a controller box and one or more containers/reservoirs,
said one or more containers/reservoirs disposed almost entirely in the controller box,
the one or more containers/reservoirs having at least one or more open ends and one or more luer locks associated with the one or more containers/reservoirs that allows the one or more containers/reservoirs to be engaged and secured to the controller box,
the controller box comprising one or more pumps disposed in the controller box that are configured to create a positive pressure within the controller box and further configured to create a negative pressure in the controller box thereby moving the one or more pistons inside the one or more containers/reservoirs,
wherein the at least one or more open ends are designed to allow passage of air and/or fluids from an area that is outside the one or more containers/reservoirs to an area inside of the one or more containers/reservoirs or from an area that is inside the one or more containers/reservoirs to an area outside of the one or more containers/reservoirs,
wherein irrigation and/or aspiration is/are prevented while the one or more pistons is/are stationary,
said passage of air and/or fluids optionally passed through one or more conduits that can be operationally attached to said one or more containers/reservoirs.

14. The apparatus of claim 13, wherein the apparatus further comprises at least one of one or more suction/ejection switches, one or more nozzles/conduits, one or more motor speed control modules, one or more batteries, one or more slots, an on/off power switch, one or more gaskets, one or more solar panels or a power connector plug.

15. The apparatus of claim 14, wherein the one or more suction/ejection switches are operationally connected to the one or more pumps so that when the one or more suction/ejection switches are switched to a suction position the one or more pistons move in a direction that performs aspiration and when the one or more suction/ejection switches are switched to an ejection position the one or more pistons move in a direction that performs irrigation.

16. The apparatus of claim 15, wherein the one or more motor speed control modules control power of the one or more pumps either increasing or decreasing an ability of the one or more pumps to aspirate and/or irrigate the ears, nasal passages, and wounds.

17. The apparatus of claim 16, wherein the one or more containers/reservoirs are of a size between 20 and 40 milliliters.

18. A method of irrigating or aspirating ears, nasal passages, and/or wounds, said method comprising:
procuring an apparatus that comprises a controller box and one or more containers/reservoirs,
said one or more containers/reservoirs disposed almost entirely in the controller box,
the one or more containers/reservoirs having at least one or more open ends and one or more luer locks associated with the one or more containers/reservoirs that allows the one or more containers/reservoirs to be engaged and secured to the controller box,
the controller box comprising one or more pumps disposed inside the controller box that are configured to create a positive pressure within the controller box and further configured to create a negative pressure in the controller box thereby moving the one or more pistons inside the one or more containers/reservoirs,
wherein the at least one or more open ends are designed to allow passage of air and/or fluids from an area that is outside the one or more containers/reservoirs to an area inside of the one or more containers/reservoirs or from an area that is inside the one or more containers/reservoirs to an area outside of the one or more containers/reservoirs,
wherein irrigation and/or aspiration is/are prevented while the one or more pistons is/are stationary,
wherein a user moves air and/or fluids from an area that is inside the one or more containers/reservoirs to an area inside the ears, nasal passages, or wounds optionally through one or more conduits that are operationally attached to the one or more containers/reservoirs, and subsequently removing the air and/or fluids from inside the ears, nasal passages, and/or wounds, thereby irrigating and/or aspirating the ears, nasal passages, and/or wounds.

19. The method of claim 18, further comprising applying antibiotics, baby oil, mineral oil, glycerin or hydrogen peroxide to the ears, nasal passages, and/or wounds using the apparatus.

20. The method of claim 18, wherein the method is performed at least twice.

21. The method of claim 18, wherein the controller box houses at least two containers/reservoirs, and simultaneous irrigation and aspiration of the ears, nasal passages, and/or wounds occurs.

* * * * *